(12) United States Patent
Forsell

(10) Patent No.: US 9,265,610 B2
(45) Date of Patent: Feb. 23, 2016

(54) IMPLANTABLE MEDICAL DEVICE FOR LUBRICATION OF A SYNOVIAL JOINT AND METHOD FOR IMPLANTING THE DEVICE

(76) Inventor: Peter Forsell, Bouveret (CH)

( * ) Notice: Subject to any disclaimer, the term of this patent is extended or adjusted under 35 U.S.C. 154(b) by 0 days.

(21) Appl. No.: 13/382,853

(22) PCT Filed: Jul. 12, 2010

(86) PCT No.: PCT/SE2010/050801
§ 371 (c)(1),
(2), (4) Date: Jan. 6, 2012

(87) PCT Pub. No.: WO2011/005185
PCT Pub. Date: Jan. 13, 2011

(65) Prior Publication Data
US 2012/0101456 A1    Apr. 26, 2012

Related U.S. Application Data

(60) Provisional application No. 61/229,738, filed on Jul. 30, 2009, provisional application No. 61/229,739, filed on Jul. 30, 2009, provisional application No.
(Continued)

(30) Foreign Application Priority Data

| | | | |
|---|---|---|---|
| Jul. 10, 2009 | (SE) | ...................................... | 0900957 |
| Jul. 10, 2009 | (SE) | ...................................... | 0900958 |
| Jul. 10, 2009 | (SE) | ...................................... | 0900959 |
| Jul. 10, 2009 | (SE) | ...................................... | 0900960 |
| Jul. 10, 2009 | (SE) | ...................................... | 0900962 |
| Jul. 10, 2009 | (SE) | ...................................... | 0900963 |
| Jul. 10, 2009 | (SE) | ...................................... | 0900965 |
| Jul. 10, 2009 | (SE) | ...................................... | 0900966 |
| Jul. 10, 2009 | (SE) | ...................................... | 0900968 |
| Jul. 10, 2009 | (SE) | ...................................... | 0900969 |
| Jul. 10, 2009 | (SE) | ...................................... | 0900970 |
| Jul. 10, 2009 | (SE) | ...................................... | 0900972 |
| Jul. 10, 2009 | (SE) | ...................................... | 0900973 |
| Jul. 10, 2009 | (SE) | ...................................... | 0900974 |
| Jul. 10, 2009 | (SE) | ...................................... | 0900976 |
| Jul. 10, 2009 | (SE) | ...................................... | 0900978 |
| Jul. 10, 2009 | (SE) | ...................................... | 0900981 |

(51) Int. Cl.
*A61F 2/30*    (2006.01)
*A61F 2/36*    (2006.01)

(52) U.S. Cl.
CPC ............... *A61F 2/30721* (2013.01); *A61F 2/36* (2013.01); *A61F 2002/30566* (2013.01);
(Continued)

(58) Field of Classification Search
CPC ............................... A61F 2/30; A61F 2/30673
USPC .......... 623/14.12, 22.13; 604/59–64, 82, 506, 604/519
See application file for complete search history.

(56) References Cited

U.S. PATENT DOCUMENTS

| | | |
|---|---|---|
| 5,120,312 A | 6/1992 | Wigness et al. |
| 5,462,362 A | 10/1995 | Yuhta et al. |

(Continued)

OTHER PUBLICATIONS

International Search Report for PCT/SE2010/050801, mailed Oct. 20, 2010.

*Primary Examiner* — Bruce E Snow

(57) ABSTRACT

An implantable medical device for lubrication of a synovial joint having a joint cavity is provided. The implantable device comprises a solid lubricant and a feeding device, wherein said feeding device is adapted to feed said solid lubricant into the joint cavity for lubricating the synovial joint.

18 Claims, 24 Drawing Sheets

Related U.S. Application Data

61/229,743, filed on Jul. 30, 2009, provisional application No. 61/229,745, filed on Jul. 30, 2009, provisional application No. 61/229,746, filed on Jul. 30, 2009, provisional application No. 61/229,747, filed on Jul. 30, 2009, provisional application No. 61/229,748, filed on Jul. 30, 2009, provisional application No. 61/229,751, filed on Jul. 30, 2009, provisional application No. 61/229,752, filed on Jul. 30, 2009, provisional application No. 61/229,755, filed on Jul. 30, 2009, provisional application No. 61/229,761, filed on Jul. 30, 2009, provisional application No. 61/229,767, filed on Jul. 30, 2009, provisional application No. 61/229,778, filed on Jul. 30, 2009, provisional application No. 61/229,786, filed on Jul. 30, 2009, provisional application No. 61/229,789, filed on Jul. 30, 2009, provisional application No. 61/229,796, filed on Jul. 30, 2009, provisional application No. 61/229,735, filed on Jul. 30, 2009.

(52) U.S. Cl.
CPC .............. *A61F 2002/30601* (2013.01); *A61F 2002/30668* (2013.01); *A61F 2002/30673* (2013.01); *A61F 2002/30675* (2013.01)

(56) References Cited

U.S. PATENT DOCUMENTS

| | | |
|---|---|---|
| 2003/0033021 A1 | 2/2003 | Plouhar et al. |
| 2003/0060891 A1 | 3/2003 | Shah |
| 2005/0277921 A1 | 12/2005 | Ray et al. |
| 2007/0088442 A1 | 4/2007 | Cima et al. |
| 2007/0118218 A1 | 5/2007 | Hooper |
| 2011/0238016 A1* | 9/2011 | Hotchkiss et al. ............ 604/175 |
| 2013/0197444 A1* | 8/2013 | Bailleul ........................ 604/187 |
| 2014/0105852 A1* | 4/2014 | Vonwiller et al. .......... 424/78.38 |

* cited by examiner

A - A

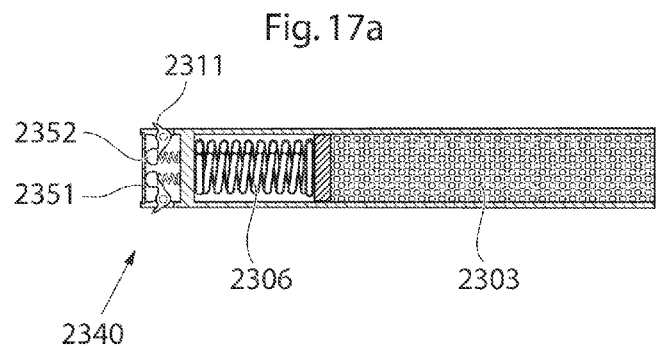
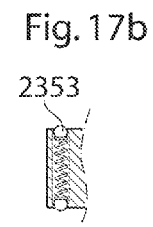
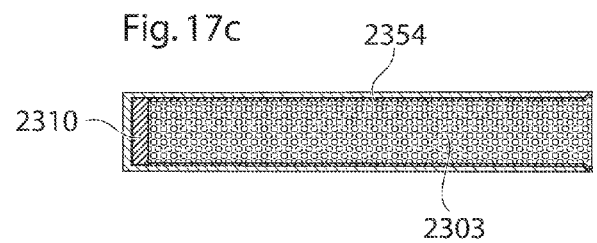
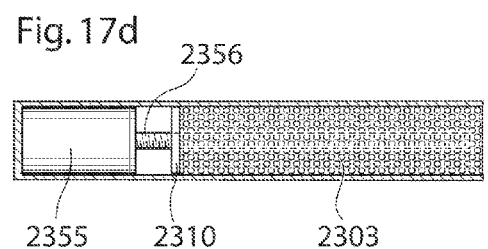
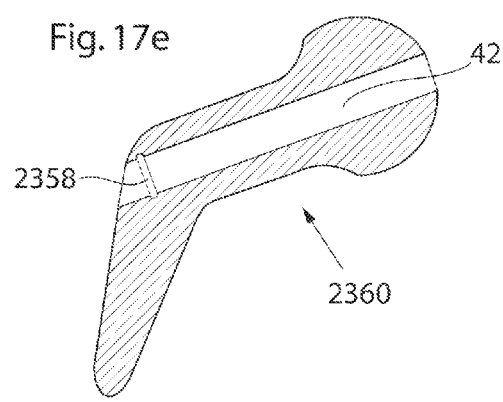

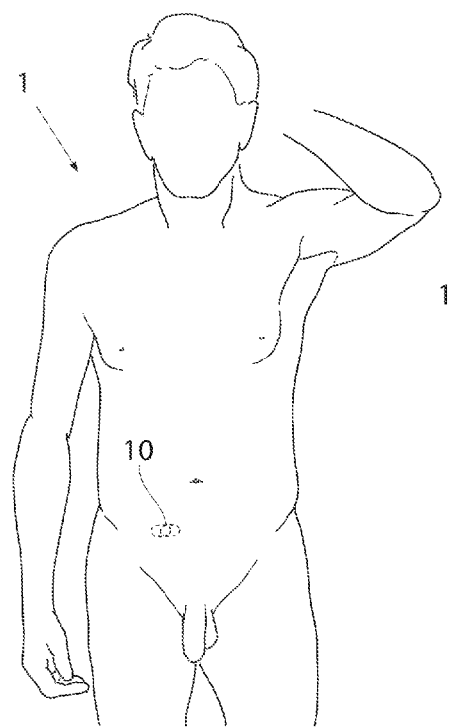
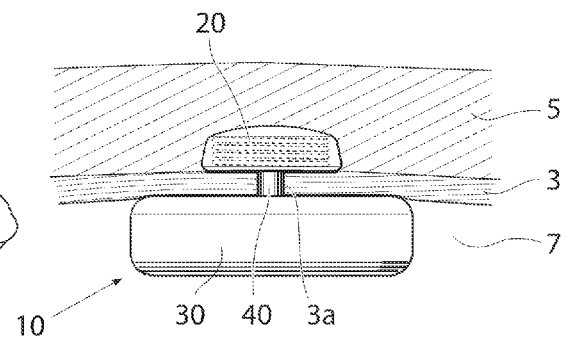
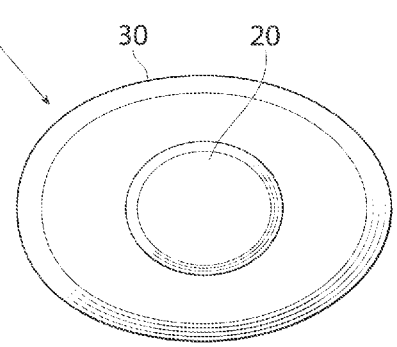
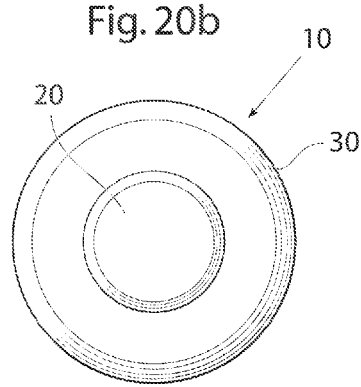
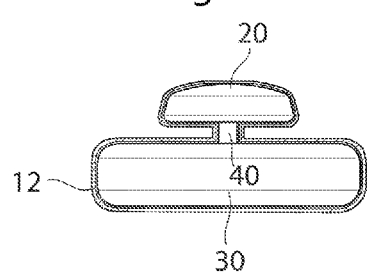

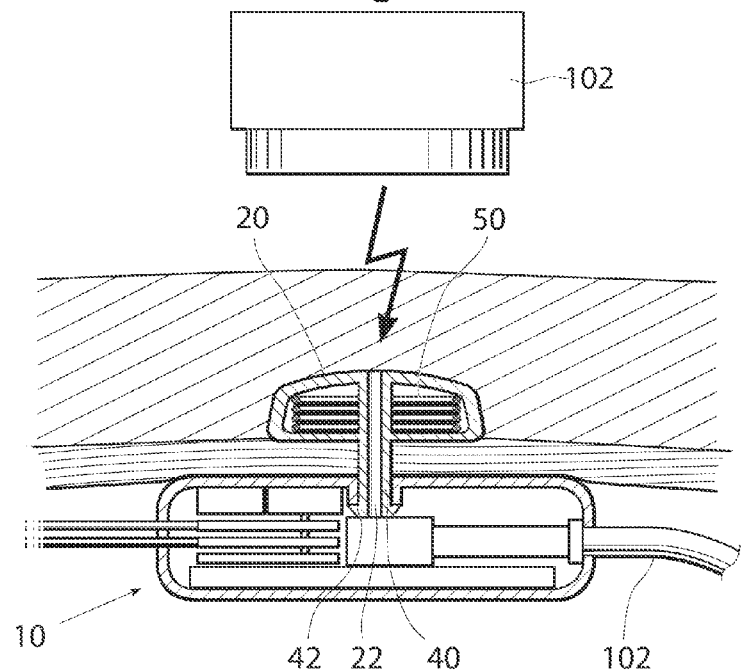
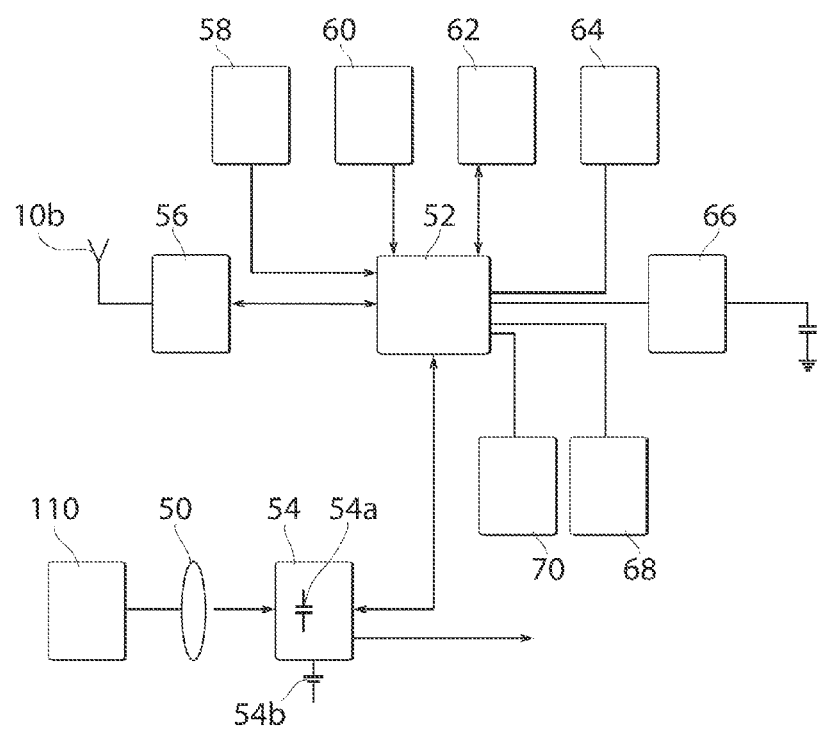

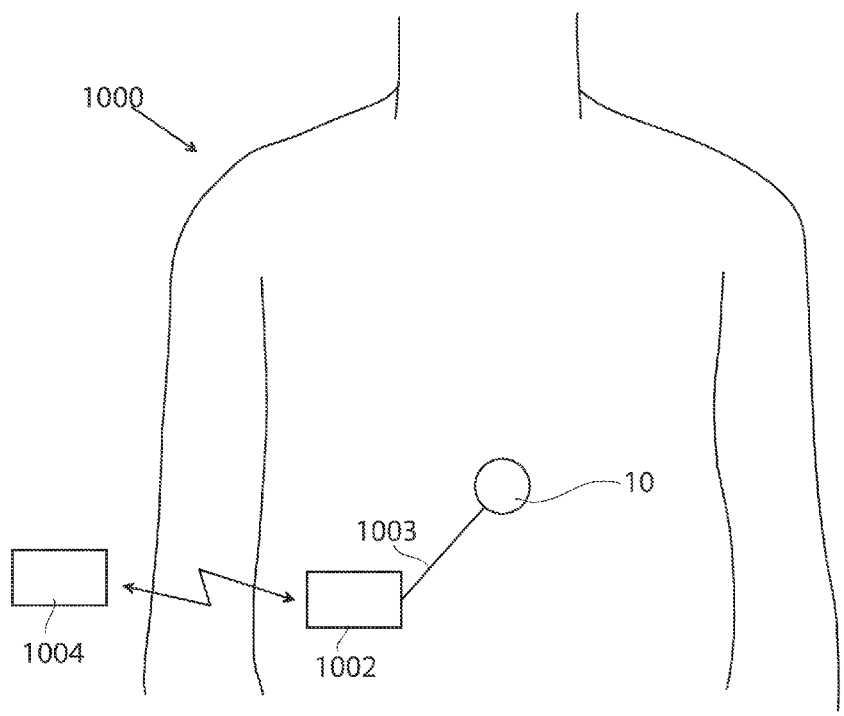

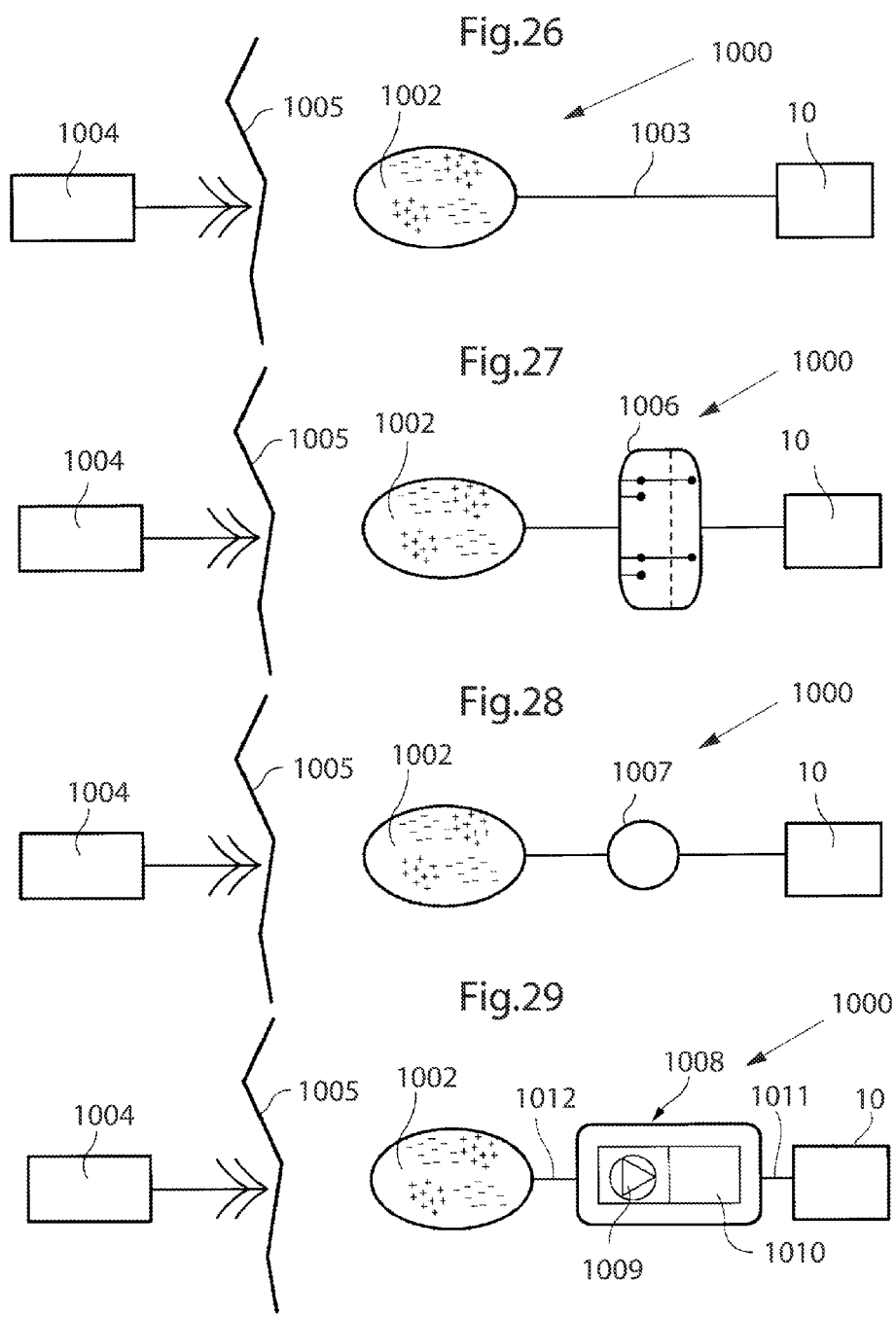

IMPLANTABLE MEDICAL DEVICE FOR LUBRICATION OF A SYNOVIAL JOINT AND METHOD FOR IMPLANTING THE DEVICE

This application is the U.S. national phase of International Application No. PCT/SE2010/050801, filed 12 Jul. 2010, which designated the U.S. and claims the benefit of U.S. Provisional Nos. 61/229,755, filed 30 Jul. 2009; 61/229,738 filed 30 Jul. 2009; 61/229,739 filed 30 Jul. 2009; 61/229,743 filed 30 Jul. 2009; 61/229,745 filed 30 Jul. 2009; 61/229,746 filed 30 Jul. 2009; 61/229,747 filed 30 Jul. 2009; 61/229,748 filed 30 Jul. 2009; 61/229,751 filed 30 Jul. 2009; 61/229,752 filed 30 Jul. 2009; 61/229,761 filed 30 Jul. 2009; 61/229,767 filed 30 Jul. 2009; 61/229,778 filed 30 Jul. 2009; 61/229,786 filed 30 Jul. 2009; 61/229,789 filed 30 Jul. 2009; 61/229,796 filed 30 Jul. 2009; 61/229,735 filed 30 Jul. 2009; and which claims priority to Swedish Application Nos.: 0900981-2 filed 10 Jul. 2009; 0900957-2 filed 10 Jul. 2009; 0900958-0 filed 10 Jul. 2009; 0900959-8 filed 10 Jul. 2009; 0900960-6 filed 10 Jul. 2009; 0900962-2 filed 10 Jul. 2009; 0900963-0 filed 10 Jul. 2009; 0900965-5 filed 10 Jul. 2009; 0900966-3 filed 10 Jul. 2009; 0900968-9 filed 10 Jul. 2009; 0900969-7 filed 10 Jul. 2009; 0900970-5 filed 10 Jul. 2009; 0900972-1 filed 10 Jul. 2009; 0900973-9 filed 10 Jul. 2009; 0900974-7 filed 10 Jul. 2009; 0900976-2 filed 10 Jul. 2009 and 0900978-8 filed 10 Jul. 2009, the entire contents of each of which are hereby incorporated by reference.

FIELD OF INVENTION

The present invention relates generally to a medical device for implantation in a joint, and a method of providing said medical device.

BACKGROUND

The synovial joints are the most common types of joints in mammals, provide free movement between the bones they join, and are typical of nearly all limb joints. They can be compared to mechanical bearings in a musculo skeletal machine. A synovial joint is the meeting point of two bones, movably arranged in relation to each other. The end surfaces of said bones are usually smooth and rounded, and covered by articular cartilage. A synovial membrane encapsulates the joint, forming a joint cavity, which contains synovial fluid. Outside the synovial membrane is a fibrous capsule and ligaments, forming an articular capsule.

A healthy joint is remarkably effective with coefficients of friction lower than those obtainable with man-made journal bearings (frictional bearings). Furthermore, the constant process of renewal and restoration of living tissue ensures that a synovial joint have a durability far superior to that of any artificial bearing. So far, no artificial joint can equal the performance of a normal human joint.

There are however both natural and pathological processes leading to deteriorated joint function. With age and wear, the articular cartilage becomes less effective as a shock absorber and a lubricated surface. Different degenerative joint diseases, such as arthritis, osteoarthritis, or osteoarthrosis, accelerate the deterioration.

Developments in material science, together with modern surgical techniques have made it possible to replace one or more of the contact surfaces, or the entire joint. Due to their weight-carrying function, hip and knee joints are most frequently addressed by surgical intervention and implantation of artificial components, or joint replacement surgery.

The lubrication of a healthy joint has been the focus of many researchers. Articular cartilage is elastic, fluid-filled, and backed by a relatively impervious layer of calcified cartilage and bone. This means that load-induced compression of cartilage will force interstitial fluid to flow laterally within the tissue and to surface through adjacent cartilage. As that area, in turn, becomes load bearing, it is partially protected by the newly expressed fluid above it. This is a special form of hydrodynamic lubrication, so-called because the dynamic motion of the bearing areas produces an aqueous layer that separates and protects the contact points.

Boundary layer lubrication is the second major low-friction characteristic of normal joints. Here, the critical factor is proposed to be a small glycoprotein called lubricin. The lubricating properties of this synovium-derived molecule are highly specific and depend on its ability to bind to articular cartilage where it retains a protective layer of water molecules. Lubricin is not effective in artificial systems and thus does not lubricate artificial joints.

Other lubricating mechanisms have been proposed; some remain under investigation. Interestingly, hyaluronic acid, the molecule that makes synovial fluid viscous (synovia means "like egg white"), has largely been excluded as a lubricant of the cartilage-on-cartilage bearing. Instead, hyaluronate lubricates a quite different site of surface contact-that of synovium on cartilage. The well-vascularized, well-innervated synovium must alternately contract and then expand to cover non-loaded cartilage surfaces as each joint moves through its normal range of motion. This process must proceed freely. Were synovial tissue to be pinched, there would be immediate pain, intraarticular bleeding, and inevitable functional compromise. The rarity of these problems testifies to the effectiveness of hyaluronate-mediated synovial lubrication.

WO 01/85179 discloses fluid compositions and methods for lubrication of mammalian joints are disclosed, including both natural and artificial fluids. Synovial fluid acts to lubricate the bearing surfaces of bones and bone-like structures which are held in frictional contact within biological joints. Such fluids may be used to treat arthritic, injured, and diseased joints. Synovial fluid containing a dextran-based hydrogel with lipids provides enhanced rheological and tribological properties of such a fluid. Phospholipids are particularly useful in dextran-based compositions for synovial fluid. One phospholipid that can be used advantageously in synovial fluid is dipalmitoyl phosphatidylcholine (DPFC).

Su et al. (Design and Mechanics Simulation of Bionic Lubrication System of Artificial Joints, Journal of Bionic Engineering, Volume 3, Issue 3, 2006) describe a new structure for artificial joints with a joint capsule which is designed to overcome the drawback of current prostheses that omit many functions of the lubricant and the joint capsule. The new structure is composed of three component: lubricant, artificial joint and artificial joint capsule. The lubricant sealed in the capsule can not only reduce the wear of the artificial joint but also prevents the wear particles leaking into the body. Thus, unexpected reactions between the wear particles and body can be avoided completely.

Radin et al. (Joint Lubrication with Artificial Lubricants, Arthritis & Rheumatism, 2005, Vol. 14, 1, 126-129) studied the joint lubricating properties, in vitro, in bovine metatarsalphalangeal joints, of silicone fluid, methyl cellulose and polyvinyl-pyrrolidone compared to buffer, serum and synovial fluid. As has been previously reported, synovial fluid was almost twice as good as serum and buffer, which are equivalent in their joint lubricating qualities. Among the three artificial lubricants tested, only polyvinyl-pyrrolidone was superior to buffer or serum as a joint lubricant at 37° C. At 55° C., both polyvinyl-pyrrolidone and methyl cellulose had the same effect. At no time was any of the artificial lubricants tested as effective at reducing joint friction as was synovial fluid. Silicone fluid was consistently an inferior joint lubricant compared with buffer or serum. It was concluded that effective joint lubrication with artificial lubricants depends on their boundary and hydrophilic properties, rather than directly on their flow characteristics Lubricants can be divided into three groups; gaseous, liquid and solid. For the purposes of this description, a solid lubricant is defined as a lubricant being solid and substantially maintaining its shape at body temperature and at a pressure and mechanical stress encountered in the mammal body, including in the joints of a mammal body.

Most solid lubricants are produced as thin solid films on sliding surfaces. They are also used as fillers in self-lubricating metallic, ceramic, and polymeric composites. In most cases, a transfer film is found on the sliding surfaces. For solid lubricant films, strong adhesion is key for long service life.

Boric acid (H3BO3) films, which provide the component surfaces with a self-replenishing solid lubricant, are formed from the reaction of the B2O3 surface (deposited by various conventional methods) on the component surface with the water present in the body of the recipient-patient. Conventional methods that can be employed to deposit either a boron, H3BO3, or B2O3 film on the annuloplasty ring component surface include vacuum evaporation (with or without ion bombardment) and simple oven curing of a thin layer over the implant surface. The self-lubricating mechanism of H3BO3 is governed by its unique layered, triclinic crystal structure which allows sheets of atoms to easily slide over each other during movement, thus minimizing component wear and friction.

When present at a sliding surface, solid lubricants function the same way as their liquid counterparts. Specifically, they shear easily to provide low friction and to prevent wear damage between the sliding surfaces. Several inorganic materials (e.g. molybdenum disulfide, graphite, hexagonal boron nitride, boric acid) can provide excellent lubrication. Most of these solids owe their lubricity to a lamellar or layered crystal structure. A few others (e.g. soft metals, polytetrafluoroethylene, polyimide, certain oxides and rare-earth fluorides, diamond and diamond-like carbons, fullerenes) can also provide lubrication although they do not have a layered crystal structure.

Certain polymers are also used as solid lubricants because the attractive properties they combine are unavailable in other solid lubricants. Polymers are particularly favored for applications where cost, weight, corrosion and biocompatibility are the major considerations. In short, solid lubricants have been around for a long time, and they have been meeting some very important and critical tribological needs.

UHMW PE is another polymer used widely in total joint replacement (Kurtz et al., 1999). Because of the very long molecules and highly entangled molecular chains, it provides better wear resistance than PTFE. However, wear of this polymer still poses a major obstacle for the longevity of the total joint replacement. Recent effort to solve these problems have increased interest in the structure, morphology, and mechanical properties of the UHMW PE and in various surface ad structural treatment processes (such as crosslinking).

(Solid lubricants and self-lubricating films, Bharat Bhushan, Modern tribology handbook, Vol. 1, 2000)

Hyaluronan or hyaluronic acid is approved by the FDA for the treatment of osteoarthritis in a method called visco supplementation. In this treatment, hyaluronan is injected through the articular capsule and the synovial membrane, into the joint cavity, supplementing the synovial fluid. While mechanically cushioning the joint, and providing a temporary analgesic effect, this treatment is nevertheless recommended only as a last alternative to surgery. The injection is difficult to perform, and painful.

The present inventor set out to develop an implantable device and method for the lubrication of joints, in particular synovial joints, including natural joints, joints comprising artificial component following partial joint replacement surgery, and complete artificial joints, following complete joint replacement surgery.

Preferably said solid lubricant comprises hyaluronan (hyaluronic acid) and optionally suitable additives. Hyaluronan is particularly preferred, as this is a nontoxic, noninflammatory biodegradable natural substance.

Hyaluronan is available in different qualities, such as relating to purity, molecular weight and degree of crosslinking. With regard to molecular weight, many different qualities are available, ranging from low molecular weight (LMW) or about 50,000 Da to high molecular weight (HMW) or about 4-6,000,000 Da. An increase in molecular weight results in corresponding increase in viscosity, from an oily liquid to a gel-like semisolid.

For example WO 01/60868 discloses single phase gels for preventing the formation of surgical adhesions. The gels are prepared by reacting an aqueous solution of a polyanionic polysaccharide, such as hyaluronic acid or carboxymethyl cellulose, with divinyl sulfone, to form a gel, the solution is neutralized, and a solid is precipitated from the solution. The solid can be redissolved in water to form a gel having properties which can be modified to suit a particular application. Using a similar approach, a hyaluronic acid containing solid can be produced, and inserted in contact with the articular surfaces in a joint, where the surrounding aqueous body fluids redissolve the solid, releasing hyaluronic acid to lubricate the joint.

US 2009181058 discloses an injectable or implantable rod-shaped formulation for delivery of osteogenic proteins to treat osteoporotic and/or osteopenic bone are disclosed. The formulation comprises hyaluronic acid derivatives and osteogenic proteins, and optional excipients and active ingredients such as a bone resorption inhibitor.

WO 2006/034383 discloses viscoelastic compounds encompassing any compound having viscoelastic properties including, but not limited to, cellulose polymers and their derivatives (for example hydroxypropyl methyl cellulose) and polysaccharides including, but not limited to, glucosaminoglycans such as hyaluronic acid and synthetic linear polymers. By way of example, the viscoelastic compound may be chondroitin sulphate, polyacrylamide, collagen, pectin, synthetic polymer-modified carbohydrate, hyaluronic acid or salts or esters thereof in essentially pure form and dry form, or mixtures of two or more of these compounds.

Suitable sodium hylauronates may in one aspect have a molecular mass of at least 5-6 million before sterilization which when dissolved to a 1% (w/w) solution will obtain similar characteristics as Healon® ophthalmic viscoelastic solution (OVD) (available from Abbot Medical Optics, Inc., Santa Ana, Calif.), or when dissolved to 2.3% (w/w) will resemble Healon® 5' OVD (available from Abbot Medical Optics, Inc., Santa Ana, Calif.)). The preparation and purification of this type of sodium hyaluronate and to generate viscoelastic solutions are described in more detail in U.S. Pat. Nos. 4,141,973 and 6,086,697. Also high viscosity, high molecular mass sodium hyaluronates such as those described in U.S. Pat. No. 5,681,825 (marketed as visco elastic under the trade name Healon® GV) can be used with the present invention. One of ordinary skill in the art will realize that in other aspect of the invention, suitable sodium hylauronates may have a lower molecular mass, as low as 100,000 Da. Clearly, the desired molecular weight is dependent on the class of polymer that is desired to be used in association with the present invention. By way of example, and not of limitation, suitable viscoelastic solutions may be formed using HPMC in the weight range of from about 30,000 to about several hundred thousand daltons. Similarly, suitable viscoelastic solutions may be formed using chondroitin sulphate in the weight range starting from about 20,000 to about 30,000. In general, the molecular weight of the chosen visco elastic compound (whether it is sodium hyaluronate, HPMC or another viscoelastic) will be selected based on the desired visco elastic properties of the final solution.

Hip joint Osteoarthritis is a syndrome in which low-grade inflammation results in pain in the hip joints, caused by abnormal wearing of the Cartilage that act as a cushion inside if the hip joint. This abnormal wearing of the cartilage also results in a decrease of the joints lubricating fluid called Synovial fluid. Hip joint Osteoarthritis is estimated to affect 80% of all people over 65 years of age, in more or less serious forms.

The present treatment for hip osteoarthritis comprises NSAID drugs, local injections of Hyaluronic acid or Glucocorticoid to help lubricating the hip joint, and replacing parts of the hip joint with a prosthesis through hip joint surgery.

The replacing of parts of the hip joint is one of the most common surgeries to date performed at hundreds of thousand of patients in the world every year. The most common method comprises placing a metal prosthesis in Femur and a plastic bowl in Acetabulum. This operation is usually done through a lateral incision in the hip and upper thigh and through, Fascia Lata and the lateral muscles of the thigh. To get access to the hip joint, the supporting hip joint capsule attached to Femur and Ilium of Pelvis needs to be penetrated, making it difficult to get a fully functional joint after the surgery. Femur is then cut at the neck with a bone saw and the prosthesis is placed in femur either with bone cement or without. Acetabulum is slightly enlarged using an Acetabular reamer, and the plastic bowl is positioned using screws or bone cement.

The surgery typically requires one week of hospitalization due to the increased risk of infection. The recovery process is on average about 6 weeks, but even after this period the patient should not perform any physical activates that places large strain on the joint.

SUMMARY

An implantable medical device for lubrication of a synovial joint having a joint cavity is provided. The implantable device comprises a solid lubricant and a feeding device, wherein said feeding device is adapted to feed said solid lubricant into the joint cavity for lubricating the synovial joint.

According to one embodiment, the solid lubricant is adapted to be placed within an implantable cartridge having an opening into the joint cavity. An inner diameter of the opening could have substantially the same diameter as the inner diameter of said cartridge.

In some embodiments, the solid lubricant could have thixotropic or shear thinning properties, such that the viscosity of said solid lubricant is reduced when said solid lubricant is exposed to strain in the joint cavity.

According to other embodiments, the solid lubricant comprises high-molecular weight hyaluronic acid, which could be crosslinked high-molecular weight hyaluronic acid or hyaluronic acids of at least two different high-molecular weight, crosslinked to form a semisolid or solid gel.

According to another embodiments, the solid lubricant comprises a crosslinking agent chosen from 1, 2, 3, 4-diepoxybutane, divinyl sulfone.

The solid lubricant could be a hydrophilic polymer chosen from synthetic and natural polysaccharides, which could be selected from a group consisting of: hydroxyethyl cellulose, carboxymethyl cellulose, xanthan gum, chondroitin sulfate, heparin, protein, sulfated protein, synthetic water-soluble polymers.

According to one embodiment, the protein comprises a protein selected from a group consisting of: collagen, elastin, albumin, and globulin.

According to one embodiment, the sulfated protein could comprise a sulfated protein selected from a group consisting of: keratin sulfate, and sulfated aminoglycosaminoglycans.

According to one embodiment, the synthetic water-soluble polymer is a synthetic water-soluble polymer selected from a group consisting of polyvinyl alcohol, co-polymers of polyvinyl alcohol, and co-polymers of poly-(hydroxyethyl)methacrylate.

According to yet another embodiment, the medical device is adapted to be implanted in the area of the hip joint, such that said solid lubricant can be inserted into the joint cavity of the hip joint.

The medical device could be adapted to at least partially be implanted in the caput femur, such that the feeding device can feed the solid lubricant into the hip joint cavity, towards the acetabulum.

According to yet another embodiment, the implantable device is adapted to be inserted into a bore in the femoral bone, which could be a bore from the lateral side of the femoral bone, in the region of the major trochanter, or a bore in the pelvis, such that the feeding device can feed the solid lubricant into the hip joint cavity, towards the caput femur. The medical device could for example be adapted to be inserted into the bore in the pelvis, from the acetabulum side of the pelvic bone or from the abdominal side of the pelvic bone.

According to yet another embodiment, the implantable medical device is adapted to be implanted in the area of the knee joint, such that said solid lubricant can be inserted into the joint cavity of the knee joint.

According to yet another embodiment, the medical device is adapted to at least partially be implanted distally in the femoral bone, such that the feeding device can feed the solid lubricant into the knee joint cavity, towards the tibia bone.

According to yet another embodiment, the implantable device is adapted to be inserted into a bore in the distal portion of the femoral bone.

According to yet another embodiment, the medical device is adapted to at least partially be implanted proximally in the tibia bone, such that the feeding device can feed the solid lubricant into the knee joint cavity, towards the femoral bone.

According to yet another embodiment, the implantable device is adapted to be inserted into a bore in the proximal portion of the tibia bone.

According to yet another embodiment, the medical device is adapted to be implanted in the area of the shoulder joint, such that the solid lubricant can be inserted into the joint cavity of the shoulder joint.

According to yet another embodiment, the medical device is adapted to at least partially be implanted in the scapula bone, such that the feeding device can feed the solid lubricant into the shoulder joint cavity, towards the humerus bone, or implanted in the humerus bone, such that the feeding device can feed the solid lubricant into the shoulder joint cavity, towards the scapula bone.

According to yet another embodiment, the medical device further comprises a retention member for retaining the medical device inside of the bore, the retention member comprises at least one bone contacting portion adapted to press on the bone of the inside of the bore for retaining said medical device in the bore. The retention member could be comprises at least one spring member adapted to exert force on said at least one bone contacting portion.

The feeding device could according to one embodiment comprises an energized feeding device, which could comprise a motor.

In other embodiments, the feeding device comprises an elastic member, which could be a spring member or a member of elastic material.

According to yet another embodiment, the feeding is adapted to be powered by a pressurized gaseous fluid.

According to yet another embodiment, the medical device is adapted tie, at least partially, be placed in a prosthesis comprising at least one joint surface being adapted for implantation.

The medical device could comprise a cartridge being adapted to be exchanged when said solid lubrication housed inside said cartridge has ended.

In yet another embodiment, the medical device further comprises an implantable sleeve adapted to be placed within a bone of the patient, and further adapted to receive said implantable medical device.

A method for improving the lubrication of a synovial joint of a patient is further provided. The method comprises the steps of drilling or punching a chamber in a bone of the patient, such that an opening of the chamber is located in the joint cavity, and implanting a medical device into the chamber comprising a solid lubricant.

In one embodiment, the method further comprises the step of implanting a feeding device adapted to feed said solid lubricant into the joint cavity for lubricating the synovial joint.

According to some embodiments the solid lubricant is housed within a cartridge, and the step of implanting the medical device could comprise the step of implanting said cartridge into the chamber.

In some embodiments, the step of drilling or punching a chamber in a bone of the patient could comprise the step of drilling or punching a chamber in a bone in the area of the hip joint, such that said solid lubricant can be inserted into the joint cavity of the hip joint. The area of the hip joint could be in the caput femur or in pelvis.

According to one embodiment, the step of implanting said cartridge into the chamber could comprise the step of implanting the cartridge into a bore created in the caput femur, such that the feeding device can feed the solid lubricant into the hip joint cavity, towards the acetabulum.

According to yet another embodiment, the step of implanting the cartridge into a bore could comprise the step of implanting the medical device into the bore from the lateral side of the femoral bone, in the region of the major trochanter.

The step of implanting the cartridge into the chamber could comprise the step of implanting the cartridge into pelvis from the abdominal side of the pelvis, such that the feeding device can feed the solid lubricant into the hip joint cavity, towards the caput femur.

In yet another embodiment, the step of drilling or punching a chamber in a bone of the patient could comprise the step of drilling or punching a chamber in a bone in the area of the knee joint, such that said solid lubricant can be inserted into the joint cavity of the knee joint.

The step drilling or punching a chamber in a bone of the patient comprises the step of drilling or punching a chamber in the femoral bone or the tibia bone.

In yet another embodiment, the step of implanting the cartridge into the chamber could comprise the step of implanting the cartridge into a bore created in the femoral bone, such that the feeding device can feed the solid lubricant into the knee joint cavity.

The step of implanting the cartridge into the chamber could comprise the step of implanting the cartridge into a bore created in the tibia bone, such that the feeding device can feed the solid lubricant into the knee joint cavity.

The step of drilling or punching a chamber in a bone of the patient could comprise the step of drilling or punching a chamber in a bone in the area of the shoulder joint, such that said solid lubricant can be inserted into the joint cavity of the shoulder joint, and the step of drilling or punching a chamber in a bone of the patient could comprise the step of drilling or punching a chamber in the humerus bone or in the scapula bone.

In yet other embodiments, the step of implanting the cartridge into the chamber could comprise the step of implanting said cartridge into a bore created in the humerus bone, such that the feeding device can feed the solid lubricant into the shoulder joint cavity.

The step of implanting the cartridge into the chamber could comprise the step of implanting the cartridge into a bore created in the scapula bone, such that the feeding device can feed the solid lubricant into the shoulder joint cavity.

According to yet another embodiment, the method further comprises the step of implanting a retention member for retaining the medical device inside of said chamber. The step of implanting the retention member could comprise the step of implanting the retention member such that the retention member presses on the bone of the inside of the bore for retaining said medical device in the bore.

The step of implanting a feeding device could comprise the step of implanting an energized feeding device, which in a further step could be connected.

The method could further comprise the step of implanting a prosthesis comprising at least one joint surface being adapted for implantation.

In yet another embodiment, the method could comprise the steps of creating an incision in the patient, removing the implanted medical device from the patient, and inserting a new medical device, and suturing or stapling the incision.

Please note that any embodiment or part of embodiment, feature, method, associated system, part of system described herein may be combined in any way.

BRIEF DESCRIPTION OF DRAWINGS

The embodiments are now described, by way of example, with reference to the accompanying drawings, in which:

FIG. 17a shows a sectional view of the medical device/cartridge according to one embodiment;

FIG. 17b shows an alternative embodiment of the retention members;

FIG. 17c shows a sectional view of the medical device/cartridge according to another embodiment;

FIG. 17d shows a sectional view of the medical device/cartridge according to an energized embodiment;

FIG. 17e shows a sectional view of a prosthetic part adapted to replace a portion of the femoral bone;

FIG. 18 is an overall view of a human patients body showing the position of an implanted assembly according to the invention;

FIG. 19 is a side view of a first embodiment of an implanted assembly according to the invention mounted to a body tissue;

FIG. 20a is a top view of the assembly shown in FIG. 19 having elliptical shape;

FIG. 20b is a top view of the assembly shown in FIG. 19 having circular shape;

FIG. 20c is a sectional view of the assembly shown in FIG. 20b;

FIG. 23 is a sectional view of the control assembly shown in FIG. 19;

FIG. 24 is a block diagram showing the different park of a control assembly according to the invention;

FIG. 25 is a side view of an alternative embodiment of an implanted assembly according to the invention comprising an injection port; and FIG. 26 is a side view of yet an alternative embodiment of an implanted assembly according to the invention comprising a pump.

FIG. 27 illustrates a system for treating a disease, wherein the system includes an implanted assembly of the invention implanted in a patient.

FIGS. 28-42 schematically show various embodiments of the system for wirelessly powering the implanted assembly shown in FIG. 1.

DETAILED DESCRIPTION

Figure 1A:
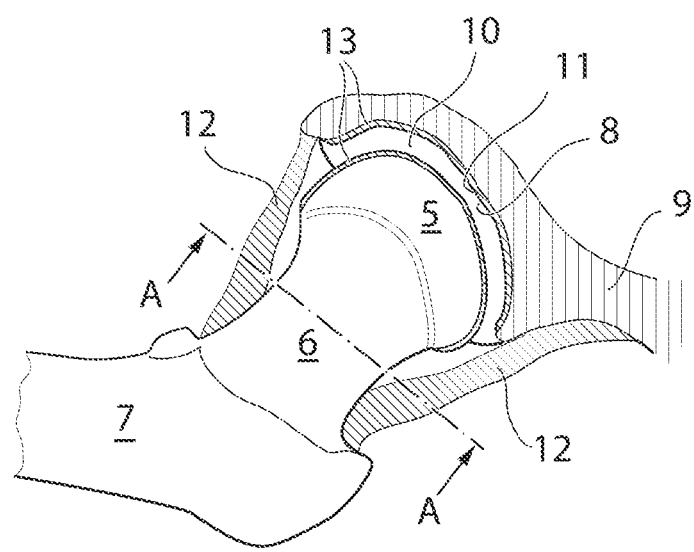
FIG. 1a is a sectional view of a hip joint.

Biocompatible material is to be understood as being a material with low level of immune response. Biocompatible materials are sometimes also referred to as biomaterials. Analogous is biocompatible metals a metal with low immune response such as titanium or tantalum. The biocompatible metal could also be a biocompatible alloy comprising at least one biocompatible metal.

Form fitting is to be understood as an element having a part or section which is adapted to enable a mechanical connection of said element to at least one other element using said part or section. Form fitted structure is a structure of an element which enables form fitting.

Elasticity is to be understood as a materials ability to deform in an elastic way.

Elastic deformation is when a material deforms under stress (e.g. external forces), but returns to its original shape when the stress is removed. A more elastic material is to be understood as a material having a lower modulus of elasticity. The elastic modulus of an object is defined as the slope of its stress-strain curve in the elastic deformation region. The elastic modulus is calculated as stress/strain, where stress is the force causing the deformation, divided by the area to which the force is applied; and strain is the ratio of the change caused by the stress.

Stiffness is to be understood as the resistance of an elastic body to deformation by an applied force.

Functional hip movements are to be understood as movements of the hip that at least partly correspond to the natural movements of the hip. On some occasions the natural movements of the hip joint might be somewhat limited or altered after hip joint surgery, which makes the functional hip movements of a hip joint with artificial surfaces somewhat different than the functional hip movements of a natural hip joint.

The functional position of an implantable medical device or prosthesis is the position in which the hip joint can perform functional hip movements.

Functional hip joint is a hip joint that can perform functional hip movements either with or without an implanted medical device or prosthesis.

In the following a detailed description of embodiments will be given. In the drawing figures, like reference numerals designate identical or corresponding elements throughout the several figures. It will be appreciated that these figures are for illustration only and are not in any way restricting the scope. Thus, any references to direction, such as "up" or "down", are only referring to the directions shown in the figures. Also, any dimensions etc. shown in the figures are for illustration purposes.

The functional position or normal functional position, of an implantable medical device or prosthesis is the position in which the hip joint can perform functional hip movements. The final position is to be understood as a functional position in which the medical device needs no further position change.

The medical device according to any of the embodiments could comprise at least one material selected from a group consisting of: polytetrafluoroethylene (PTFE), perfluoroalkoxy (PFA) and fluorinated ethylene propylene (FEP). It is furthermore conceivable that the material comprises a metal alloy, such as cobalt-chromium-molybdenum or titanium or stainless steel, or polyethylene, such as cross-linked polyethylene or gas sterilized polyethylene. The use of ceramic material is also conceivable, either solely in the contacting surfaces, or in the entire medical device, suitable ceramic materials could be zirconium or zirconium dioxide ceramics or alumina ceramics. The part of the medical device in contact with human bone for fixation of the medical device to human bone could comprise a poorhouse structure which could be a porous micro or nano-structure adapted to promote the growth-in of human bone in the medical device for fixation thereof. The porous structure could be achieved by applying a hydroxy-apatite (HA) coating, or a rough open-pored titanium coating, which could be produced by air plasma spraying, in further embodiments a combination of a rough open-pored titanium coating and a HA top layer is also conceivable. The contacting parts could according to some embodiments be made of a self lubricated material such as a waxy polymer, such as PTFE, PFA, FEP, PE and UHMW PE, or a powder metallurgy material which could be infused with a lubricant, which is preferably a biocompatible lubricant, such as a Hyaluronic acid derivate. It is also conceivable that the material of contacting parts or surfaces of the medical device herein is adapted to be constantly or intermittently lubricated in accordance with several of the embodiments disclosed herein. In yet other embodiments parts or portions of the medical device could comprise a combination of metal materials and/or carbon fibers and/or boron, a combination of metal and plastic materials, a combination of metal and carbon based material, a combination of carbon and plastic based material, a combination of flexible and stiff materials, a combination of elastic and less elastic materials, Corian or acrylic polymers.

FIG. 1 shows the hip joint of a human patient in section. The hip joint comprises a caput femur 5 placed at the very top of collum femur 6 which is the top part of the femoral bone 7. The caput femur is in connection with the acetabulum 8 which is a bowl shaped part of the pelvic bone 9. Both the caput femur surface 10 and the acetabulum surface 11 is covered with articular cartilage 13 which acts as a cushion in the hip joint. In patients with hip joint osteoarthritis, this articular cartilage 13 is abnormally worn down due to a low grade inflammation. The hip joint is surrounded by the hip joint capsule 12 which provides support for the joint and hinders luxation. After conventional hip joint surgery, penetrating the hip joint capsule 12, the capsule 12 is dramatically weakened due to the limited healing possibilities of its ligament tissue. By not having to perform a total hip joint replacement the hip joint capsule 12 can remain intact.

The femoral bone, as well as most other bones in the human body comprises cortical bone, the outer dense, sclerotic bone, and cancellous bone comprised of a less dense cell structure comprising the bone marrow.

Figure 1B:
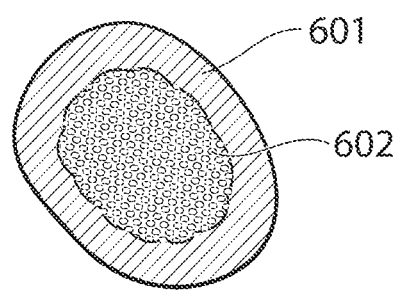
FIG. 1b is a sectional view of a collum femur.

FIG. 1b shows a cross-section of the collum femur (6 in FIG. 1a) displaying the cortical bone 601 and the cancellous bone 602, the cortical bone 601 thus enclosing the cancellous bone 602.

Figure 2:
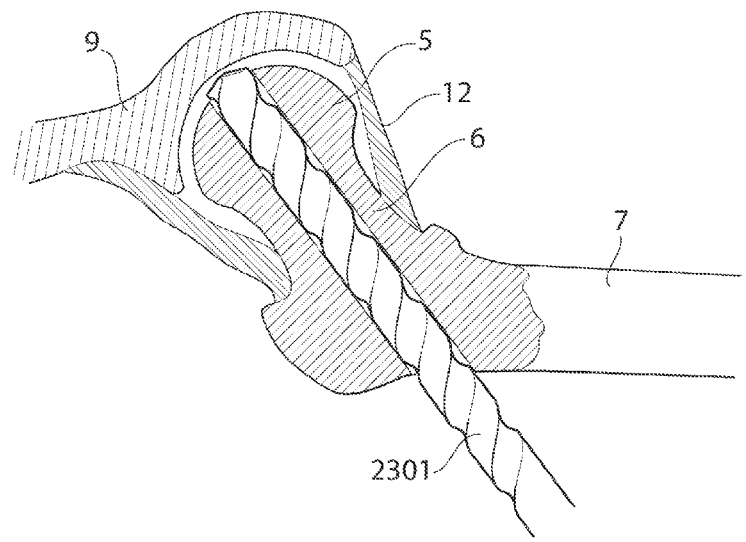
FIG. 2 is a sectional view of the femoral bone and the hip joint when a bore is created in the femoral bone 5.

FIG. 2 shows the step of creating a bore in the femoral bone from the lateral side of the thigh using an orthopedic drill 2301. The bore penetrates the most proximal part of the femoral bone, being the caput femur 5 and thus reaches the synovial area of the hip joint comprising the contacting surfaces of caput femur 5 and acetabulum 8, the synovial area being the area in which the synovial fluid is present.

Figure 3:
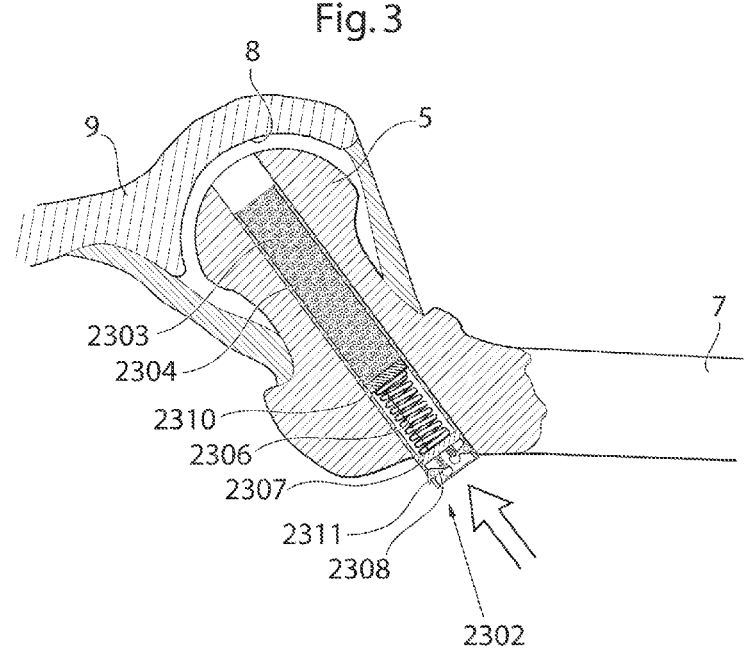
FIG. 3 is a sectional view of the femoral bone and the hip joint when a medical device is inserted into the bore in the femoral bone.

FIG. 3 shows the step of inserting an implantable device being a cartridge 2302 comprising a solid lubricant 2303 housed within the walls 2304 of the cartridge 2302. The solid lubricant being adapted to lubricate the contacting surfaces of the acetabulum 8 and the caput femur 5. The bottom portion of the cartridge 2302 comprises a feeding device adapted to feed the solid lubricant, here comprising a spring member 2306 which presses on a bottom plate 2310 disposed within the cartridge 2302, further pressing the solid lubricant 2303 through the cartridge 2302 and in the synovial area for lubricating said contacting surfaces. The spring member 2306 is in contact with the dividing wall 2307 of the cartridge, on the other side of the dividing wall 2307 of the cartridge 2302 a retention member 2308 for retaining the cartridge 2302 in the femoral bone is disposed. The retention member comprises two spring loaded bone engaging members 2311 engaging the inside of the bore when the cartridge 2302 is fully inserted into the bore and thus restrains the cartridge 2302 within the bore (shown in FIG. 4). The solid lubricant could comprise high-molecular weight hyaluronic acid. Hyaluronan is available in different qualities, such as relating to purity, molecular weight and degree of crosslinking. With regard to molecular weight, many different qualities are available, ranging from low molecular weight (LMW) or about 50,000 Da to high molecular weight (HMW) or about 4-6,000,000 Da. An increase in molecular weight result in corresponding increase in viscosity, from an oily liquid to a gel-like semisolid. Suitable sodium hylauronates may in one aspect have a molecular mass of at least 5-6 million before sterilization which when dissolved to a 1% (w/w) solution will obtain similar characteristics as Healon® ophthalmic viscoelastic solution (OVD) (available from Abbot Medical Optics, Inc., Santa Ana, Calif.), or when dissolved to 2.3% (w/w) will resemble Healon® 5' OVD (available from Abbot Medical Optics, Inc., Santa Ana, Calif.)). The preparation and purification of this type of sodium hyaluronate and to generate viscoelastic solutions are described in more detail in U.S. Pat. Nos. 4,141,973 and 6,086,697. Also high viscosity, high molecular mass sodium hyaluronates such as those described in U.S. Pat. No. 5,681,825 (marked as viscoelastic under the trade name Healon® GV) can be used with the present invention. One of ordinary skill in the art will realize that in other aspect of the invention, suitable sodium hylauronates may have a lower molecular mass, as low as 100,000 Da. Clearly, the desired molecular weight is dependent on the class of polymer that is desired to be used in association with the present invention. By way of example, and not of limitation, suitable viscoelastic solutions may be formed using HPMC in the weight range of from about 30,000 to about several hundred thousand daltons. Similarly, suitable viscoelastic solutions may be formed using chondroitin sulphate in the weight range starting from about 20,000 to about 30,000. In general, the molecular weight of the chosen viscoelastic compound (whether it is sodium hyaluronate, HPMC or another viscoelastic) will be selected based on the desired viscoelastic properties of the final solution.

The solid lubricant could comprise a crosslinking agent chosen from 1, 2, 3, 4-diepoxybutane, divinyl sulfone further containing a hydrophilic polymer chosen from synthetic and natural polysaccharides, such as hydroxyethyl cellulose, carboxymethyl cellulose, xanthan gum, chondroitin sulfate, heparin, proteins of various types, such as collagen, elastin, albumin, a globulin, etc., or sulfated pro bins such as keratin sulfate and sulfated aminoglycosaminoglycans, synthetic water-soluble polymers, such as polyvinyl alcohol and its co-polymers, co-polymers of poly-(hydroxyethyl)methacrylate and the like.

Figure 4:
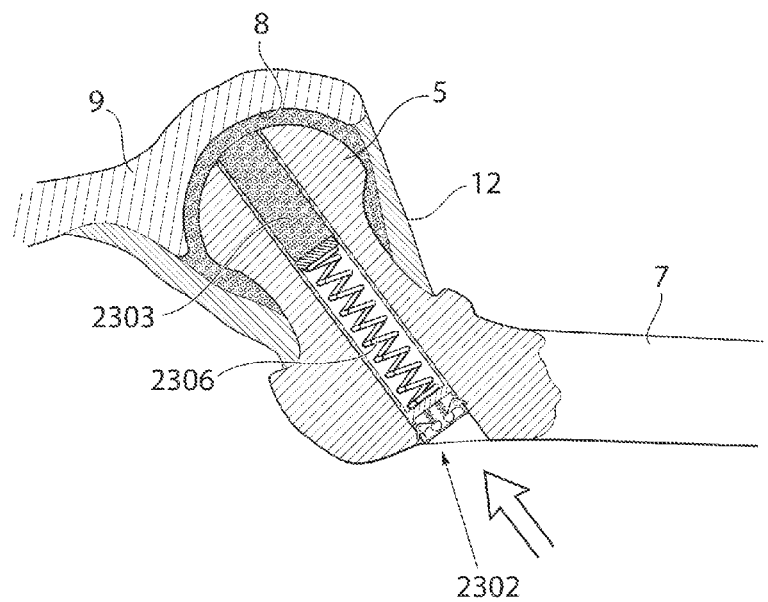
FIG. 4 is a sectional view of the femoral bone and the hip joint when the solid lubricant has been pressed into the cavity of the hip joint.

FIG. 4 shows the implantable medical device when a portion of the solid lubricant 2303 has been pressed into the synovial area of the hip for lubricating the hip joint. The spring loaded cartridge maintains a pressure in the synovial area and as some of the solid lubricant over time is resorbed by, or diffuses through the encapsulating tissue of the hip joint, new lubricant is added from the portion still housed within the cartridge by means of the spring member 2306.

According to one embodiment the solid lubricant has thixotropic or shear thinning properties such that the strain which is placed on the exposed portion of the solid lubricant alters the viscosity of the solid lubricant for creating a well functioning lubricant.

Figure 5A:
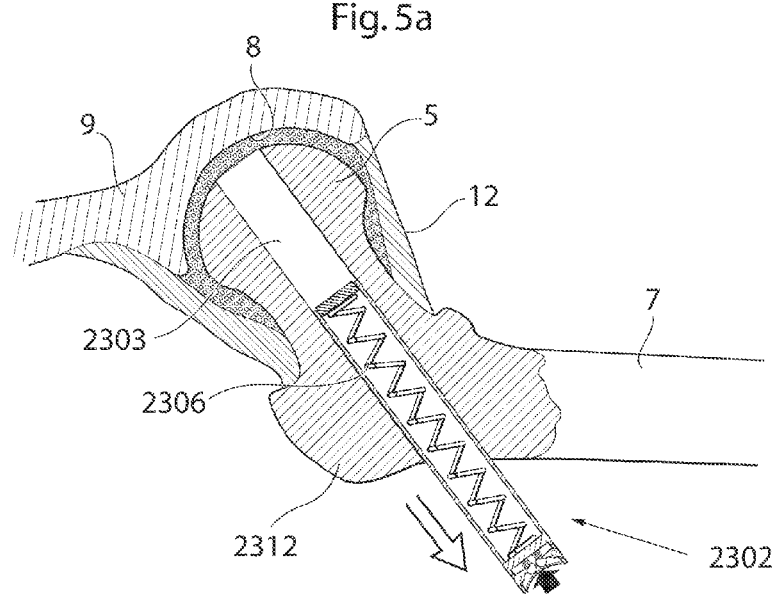
FIG. 5a is a sectional view of the femoral bone and the hip joint when the medical device/cartridge is being removed from the bore in the femoral bone.

FIG. 5a shows the hip joint in section when the all of the solid lubricant in the cartridge 2302 has been pressed into the synovial area of the joint. Depending on the degree of damage on the joint and the particular patient this could take from a number of weeks to several years, after which the cartridge 2302 needs to be replaced or refilled. In FIG. 5 the process of removing the cartridge 2302 is shown. An incision has been performed on the lateral side of the thigh, beneath the greater trochanter 2312, through which incision the cartridge 2302 can be removed.

Figure 5B:
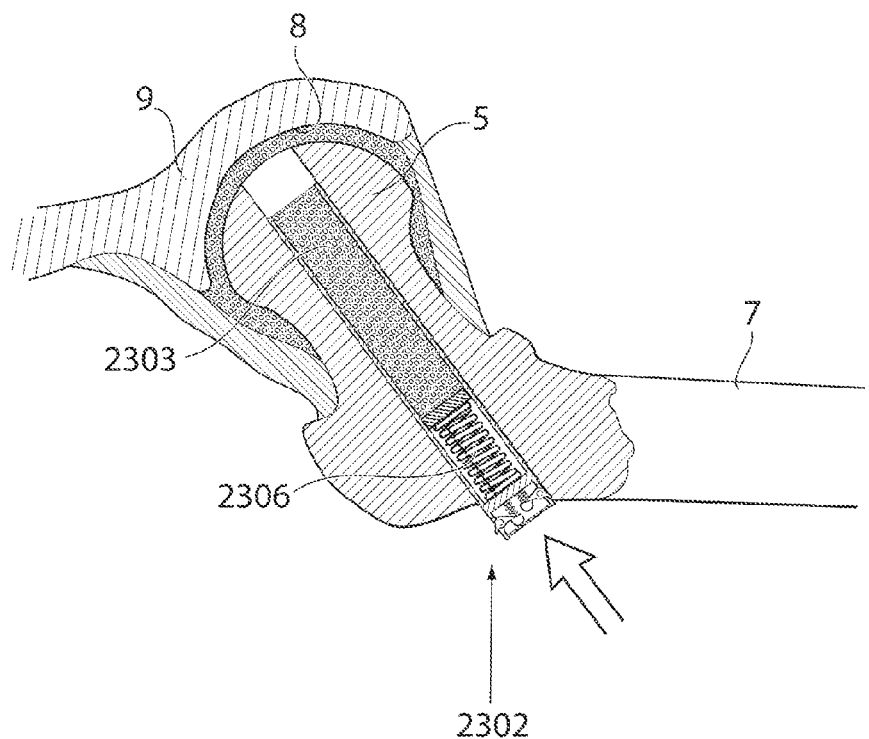
FIG. 5b is a sectional view of the femoral bone and the hip joint when a replacement cartridge is placed in the bore.

FIG. 5b shows the placing of a replacement cartridge 2302 into the bore. The replacement cartridge 2302 carries more solid lubricant 2303 adapted to lubricate the joint surfaces of the hip joint.

Figure 6:
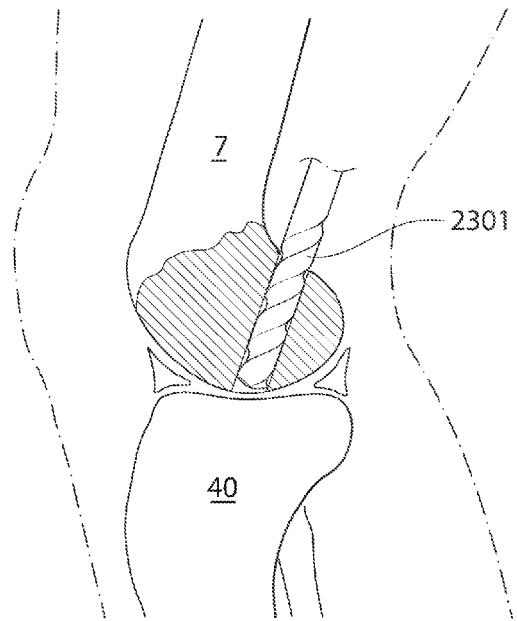
FIG. 6 shows the creation of a bore in the distal part of the femoral bone.

FIGS. 6-10 shows an embodiment in which the principle disclosed with reference to FIGS. 2-5 is applied to the knee of a patient. FIG. 6 shows the creation of a bore in the distal part of the femoral bone 7 using an orthopedic drill 2301. The bore is created through an incision from the posterior side of the femoral bone 7. The bore reaches the surfaces of the knee joint, i.e. the distal surface of the femoral bone 5 and the proximal surface of the tibia bone 40.

Figure 7:
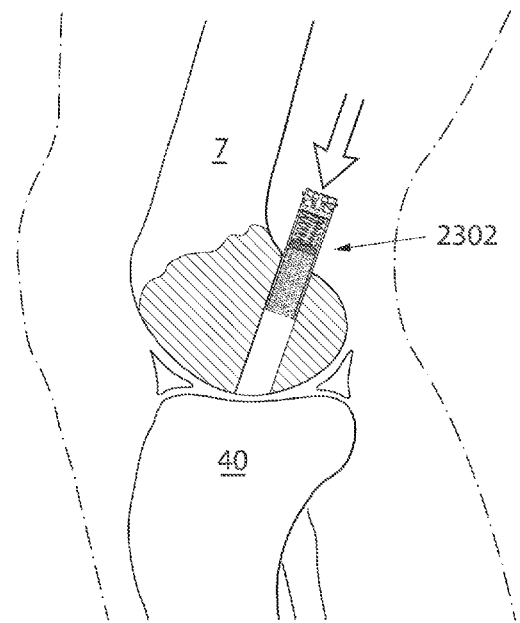
FIG. 7 shows the placing of a cartridge in the distal part of the femoral bone.

FIG. 7 shows the insertion of a cartridge 2302, according to any of the embodiments disclosed herein, in the bore created in the distal portion of the femoral bone 7.

Figure 8:
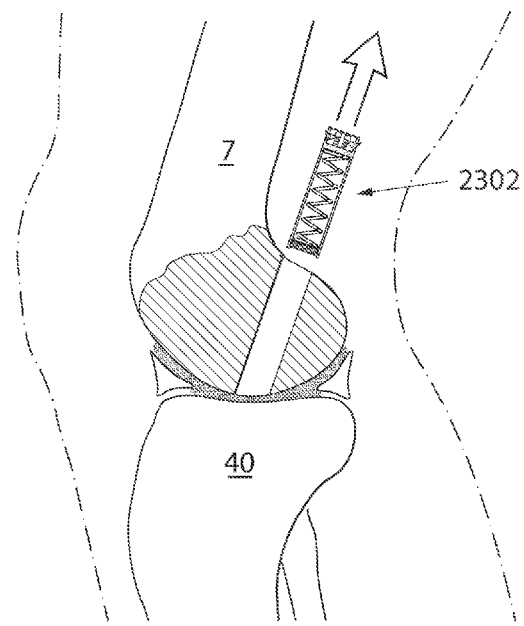
FIG. 8 shows the removal of a cartridge in the distal part of the femoral bone.

FIG. 8 shows the removal of the cartridge from the bore in the femoral bone 7, after the cartridge 2302 has been used such that little or no solid lubricant 2303 remains in the cartridge 2302.

Figure 9A:
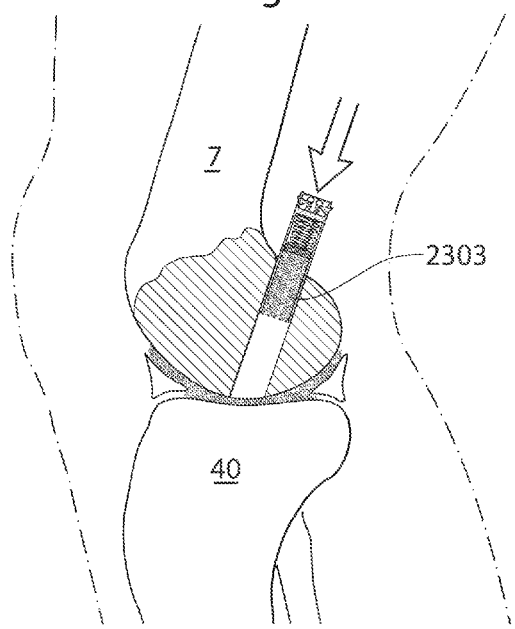
FIG. 9a shows the placing of a replacement cartridge in the distal part of the femoral bone.

FIG. 9a shows the placing of a replacement cartridge 2302 into the bore. The replacement cartridge 2302 carries more solid lubricant 2303 adapted to lubricate the joint surfaces of the knee joint.

Figure 9B:
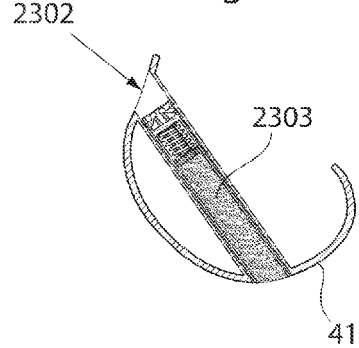
FIG. 9b shows a prosthetic part having a bore in which the medical device is adapted to be placed.

FIG. 9b shows the cartridge 2302 when inserted into a prosthetic hip joint surface 41 adapted to replace the contacting surface of the femoral bone 7. The medical device here being adapted to lubricate the surface between the prosthetic hip joint surface 41 and the natural hip joint surface of the tibia bone 40 or another prosthetic surface adapted to replace the tibia 40 contacting surface.

Figure 10:
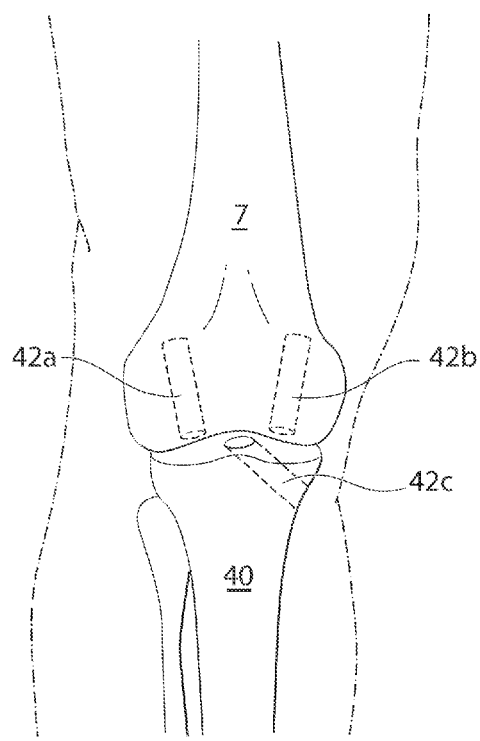
FIG. 10 shows bore locations in the femoral and tibia bone.

FIG. 10 shows the femoral bone 7 and tibia bone 40 in a frontal view. Two bores 42a,b have been made in the femoral bone 7 and one bore 42c has been made in the tibia bone. These bores are examples of different locations in which the medical devices can be placed. In some embodiments in is further conceivable that several medical devices are needed to lubricate one joint.

Figure 11:
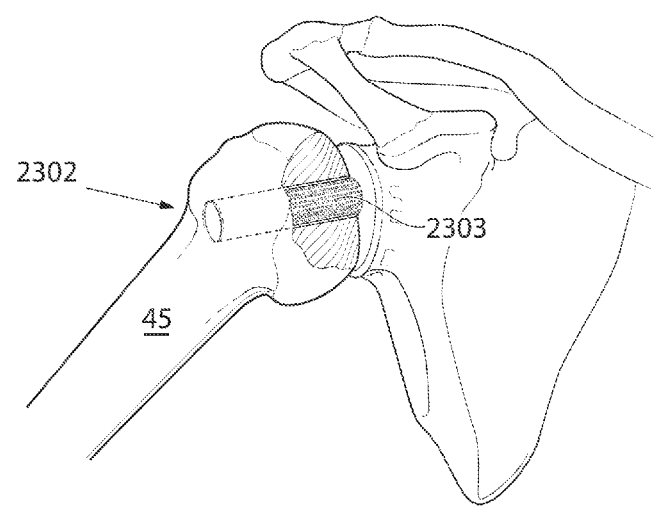
FIG. 11 shows the medical device when placed in a bore in the humerus bone.

FIG. 11 shows an embodiment in which the cartridge 2302, according to any of the embodiments herein, containing the solid lubricant 2303, is placed in a bore in the humerus bone 45 for lubricating the shoulder joint of a patient using the solid lubricant.

Figure 12:
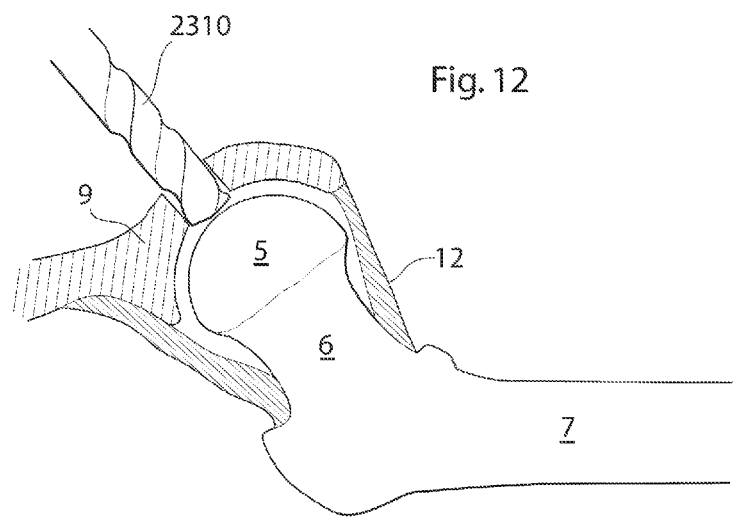
FIG. 12 shows the creation of a bore in the pelvic bone from the abdominal side of the pelvic bone.

FIG. 12 shows the hip joint in section in an embodiment in which a bore is created in the pelvic bone 9 by means of an orthopedic drill 2301.

Figure 13:
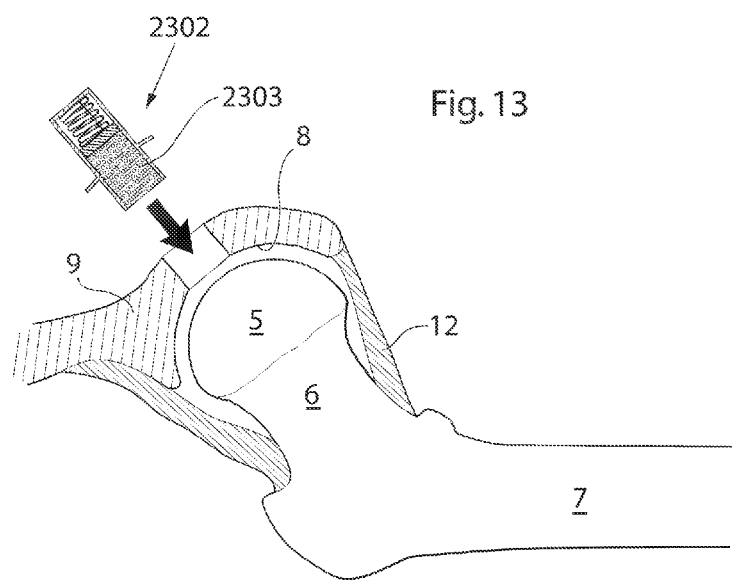
FIG. 13 shows the placing of a medical device in the bore created in the pelvic bone.

FIG. 13 shows the placing of a cartridge 2302 containing solid lubricant 2303 in the pelvic bone 9. The solid lubricant 2303 is in accordance with the other embodiments disclosed herein adapted to lubricate the surfaces of acetabulum 8 and the caput femur 5.

Figure 14:
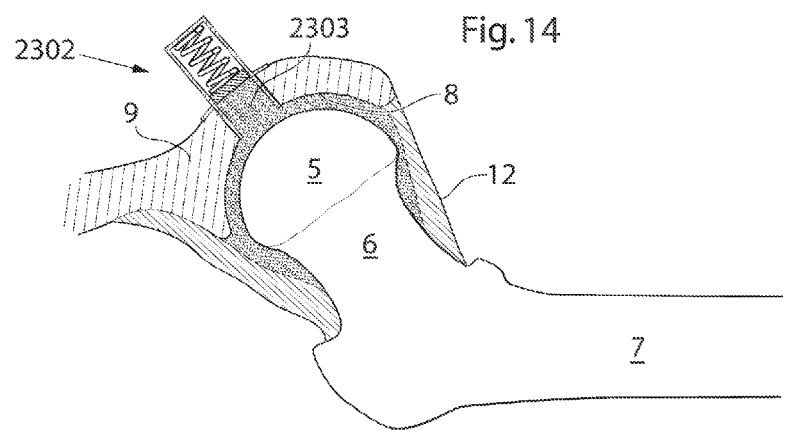
FIG. 14 shows the hip joint in section when the solid lubricant has been pressed into the hip joint cavity.

FIG. 14 shows the implantable medical device when a portion of the solid lubricant 2303 has been pressed into the synovial area of the hip for lubricating the hip joint. The spring loaded cartridge 2302 maintains a pressure in the synovial area and as some of the solid lubricant over time is resorbed by, or diffuses through the encapsulating tissue of the hip joint, new lubricant is added from the portion still housed within the cartridge by means of the spring member 2306.

According to one embodiment the solid lubricant has thixotropic or shear thinning properties such that the strain which is placed on the exposed portion of the solid lubricant alters the viscosity of the solid lubricant for creating a well functioning lubricant.

Figure 15:
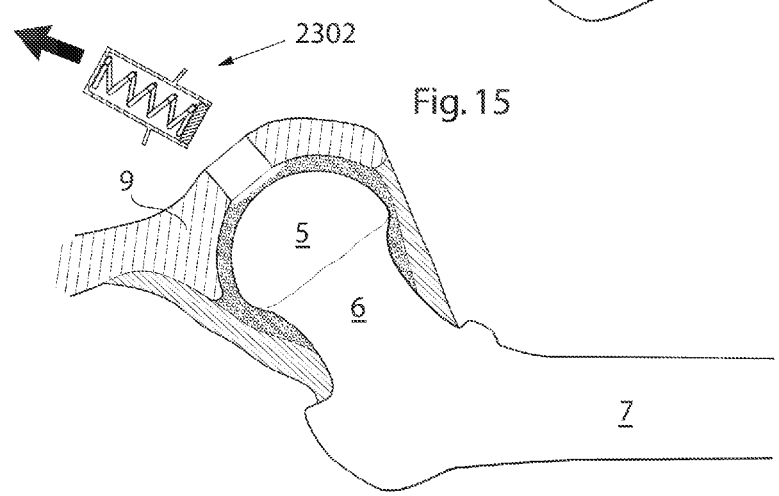
FIG. 15 shows the removal of the medical device in the direction of the abdominal cavity.

FIG. 15 shows the hip joint in section when the all of the solid lubricant in the cartridge 2302 has been pressed into the synovial area of the joint. Depending on the degree of damage on the joint and the particular patient this could take from a number of weeks to several years, after which the cartridge 2302 needs to be replaced or refilled. In FIG. 15 the process of removing the cartridge 2302 through the abdominal cavity is shown.

Figure 16:
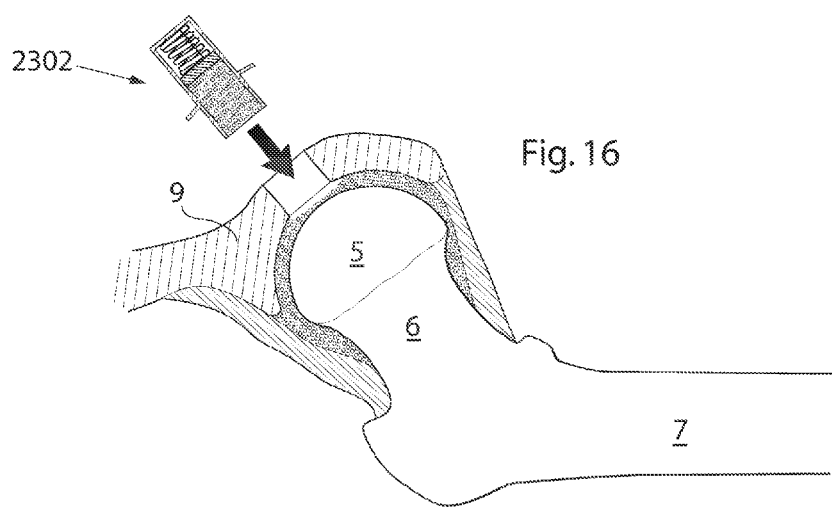
FIG. 16 shows the placing of a replacement cartridge in the bore in the pelvis, from the abdominal side of the pelvic bone.

FIG. 16 shows the placing of a replacement cartridge 2302 into the bore. The replacement cartridge 2302 carries more solid lubricant 2303 adapted to lubricate the joint surfaces of the hip joint.

FIGS. 17a-17e shows the cartridges in further detail. FIG. 17a shows an embodiment in which the cartridge comprises an ejection device 2340 for affecting the retention member comprising a resilient membrane 2351 affecting to spring loaded members 2352 which in turn affects bone engaging members 2311. In normal operation the bone engaging members 2311 makes sure that the cartridge remains secured in the bore, and when the resilient member is pressed the bone engaging members 2311 folds such that the cartridge can be removed from the bore.

FIG. 17b shows an alternative embodiment of the retention member comprising bone engaging members 2353, in which the bone engaging members 2353 are adapted to be placed in a grove in the bore for retaining the cartridge inside the bore. The alternative bone engaging members 2353 are spring loaded in radial direction and the FIG. 17c shows an alternative embodiment in which the feeding device comprises elastic members 2354, preferably made from elastic material, propels the bottom plate 2310 feeding the solid lubricant 2303, out of the cartridge.

FIG. 17d shows the medical device according to an embodiment comprising a feeding device in which the bottom plate 2310 is propelled by an energized operation device, such as an electric motor 2355. The electric motor is connected to the bottom plate 2310 by means of a threaded member 2356 engaging a corresponding threaded part of the motor 2355.

FIG. 17e shows an embodiment of a prosthetic part 2360 adapted to be fixated to the femoral bone and replace the contacting surface of the caput femur. The prosthetic part 2360 is adapted to receive the medical device according to any of the embodiments herein in a bore 42 in the prosthetic part 2360. The prosthetic part 2360 comprises a groove 2358 in the bore 42 adapted to receive the bone engaging members 2353 according to the embodiment disclosed in FIG. 17b for retaining the medical device or cartridge in the bore 42.

In embodiments where the medical device comprises an energized unit, such as the motor 2355 disclosed with reference to FIG. 17d a unit for powering and/or controlling the medical device could be necessary, an example of such a unit suitable for this purpose will now be disclosed. The unit is preferably connected to the medical device by means of electrical leads and/or hydraulic conduits.

The term "functional parts" is to be interpreted as all parts of the control assembly for the electrical or hydraulic operation of the assembly.

FIG. 18 shows the body of a human patient 1. A control assembly 1110 adapted for controlling an implanted medical device is shown subcutaneously implanted in the abdominal area of the patients body. Although a specific position for the control assembly is shown in the figure, it will be appreciated that the control assembly can be provided essentially anywhere in the patients body, preferably relatively close to the implanted medical device which it is adapted to control. Generally speaking, the energy receiver 1110 may be placed in the abdomen, thorax, muscle fascia (e.g. in the abdominal wall), subcutaneously, or at any other suitable location.

An overall side view of the control assembly 1110 is shown in FIG. 19. The control assembly comprises a first unit 120 subcutaneously implanted at a first side of a body tissue 103 in the patient, such as the rectus abdominis muscle running vertically on each side of the anterior wall of the human abdomen. In other words, the first unit is positioned between the skin 105 of the patient and the body tissue 103.

A second unit 130 is implanted in a body cavity 107 of the patient at a second side of the body tissue 103, i.e., that the side opposite of the side at which the first unit 120 is provided.

The first 130 and/or second units 140 preferably have circular or elliptical cross-sectional shape when viewed from outside the patients body, see FIGS. 20a, 20b, showing a top view of the assembly having elliptical and circular shape, respectively. Combined with a smoothly curved sectional shape, this avoids any sharp corners on the units 130, 140, which could cause injuries to the patient in which the control assembly 1110 is implanted.

An interconnecting device 140 constitutes a mechanical interconnection between the first and second units 120, 130 so that the assembly 1110 is kept in place by the body tissue 103. The interconnecting device has a cross-sectional area which is smaller than the cross-sectional area of the first unit and the second unit in a plane parallel to the extension of the body tissue. In this way, a hole 103a in the body tissue 103 through which the interconnecting device 140 extends can be sufficiently small so that it is avoided that one or the other of the units 1110, 120 "slips through" the body tissue 103. Also, the cross-sectional shape of the interconnecting device 1040 is preferably circular so as to avoid damage to the body tissue 103.

The interconnection device 140 can be integral with one of the first and second units 1110, 120. Alternatively, the interconnection device 140 is a separate part, which is connected to the first and second units 110, 120 during implantation of the control assembly 110.

In a preferred embodiment, the interconnection device 140 is hollow so as to house various wires, hoses etc. electrically or hydraulically interconnecting the first and second devices 120, 130.

Alternatively or additionally, the interconnection device 140 is made of an elastic material, such as rubber, so that the control assembly 110 can adapt to the movements of the patient in which it is implanted.

Figure 21:
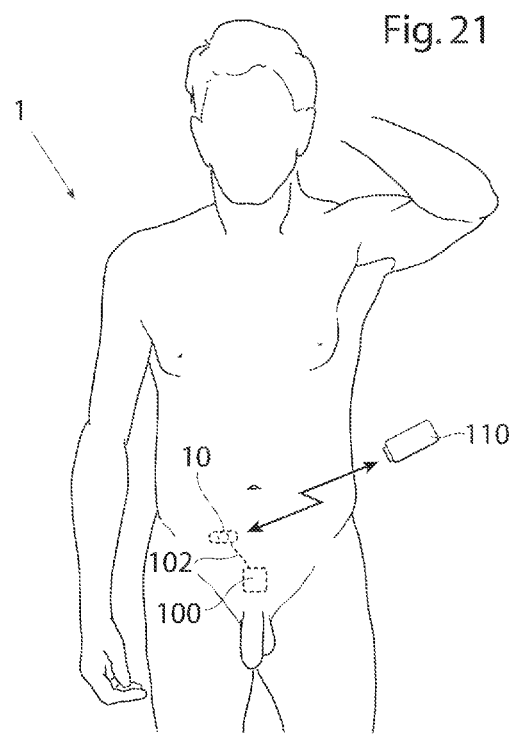
FIG. 21 is an overall view of a human patients body showing an implanted assembly according to the invention connected to an implanted medical device.

The control assembly 1110 is adapted to control a powered implanted medical device 100, see FIG. 21. The implanted medical device can be any kind of powered operation device, such as a hydraulically, pneumatically or mechanically powered operation device, such as the motor disclosed with reference to FIG. 17d. The medical device 100 can be any kind of implant, such as a constriction device adapted to constrict and release a bodily lumen or vessel, a stimulation device adapted to electrically stimulate a bodily organ, an inflatable device adapted to fill for example the corpora cavernosa of the patient etc. The implanted medical device is preferably very small, having a diameter of less than 5 centimeters, to fit in the different target areas of the body.

Depending of the kind of power required to control the medical device 100, an interconnection 102 in the form of an electrical wire, a pneumatic hose etc., is provided between the control assembly 10 and the medical device 102.

The control unit 10 is adapted to receive energy, preferably wireless energy, transmitted from an external energy source or energizer 110 located outside the skin in the vicinity of the control unit 10. The energizer 110, which is an external device which functions as the charging equipment and control device for the control assembly, is connected via a connection, such as a serial RS232 connection, to a computer 112, such as a standard desktop PC or a laptop computer. The PC software implements the user interface to the implant system, and function as the control unit and read back unit of the implant system.

Figure 22:
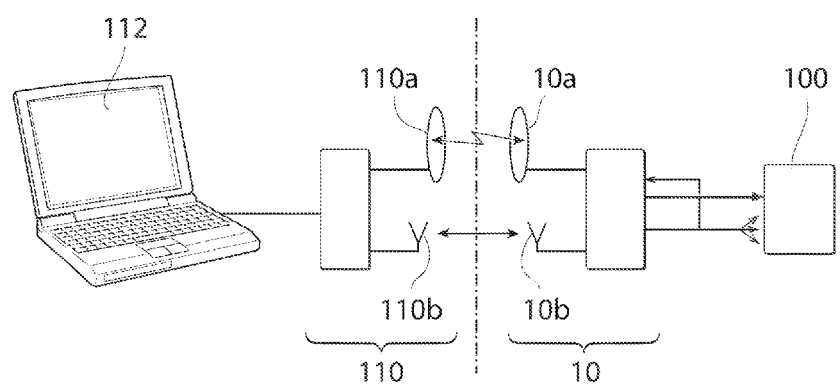
FIG. 22 is a block diagram of a control system comprising a control assembly according to the invention.

A block diagram of the implant system is shown in FIG. 22. Energy is transferred by means of the wireless coupling between an energizer coil 110a forming part of the energizer 110 and a control assembly coil 10a forming part of the control assembly 10. Similarly, control information is transferred between the energizer 110 by means of a wireless communications interface comprising an energizer antenna 110b forming part of the energizer 110 and a control assembly antenna 10b forming part of the control assembly 10. In this way, both energy and communication information can be transferred wirelessly to and from the control assembly 10.

Although separate devices are shown for transfer of energy and information, i.e., the coils and the antennas, respectively, it will be appreciated that the coils 10a, 100a can be implemented for use as an antenna as well, whereby control information can be transferred by means of the coils and no separate antennas are needed for that purpose.

The functional park of the control assembly 1110 can be provided either in the first unit 120 or in the second unit 130 or in both the first and the second unit. In other words, at least one of the first and the second unit is adapted to control a powered implanted medical device.

FIG. 23 is a sectional view of the control assembly 1110 showing an example of the contents of the first unit 120, the second unit 130 and the interconnection device 140. It is also shown that the interconnection device 140 is provided integral with the first unit 120, forming an extension from the central portion of the first unit. The outer end of the extension is provided with baths 142 engaging the rim of a hole 122 provided in the central portion of the second unit. In this way, the assembly 1110 can be assembled by a simple snap-together operation, as will be described in more detail below.

Coil 150

A coil 150 is provided in the first unit, the coil being an energy transfer coil arranged to pick up wireless electromagnetic energy and signals from an external unit. The number of rounds in the coil is adapted for the specific operation and is preferably at least ten. The end portions of the coil 150 extend perpendicularly to the general extension of the coil and are lead through the hollow interconnection device 140 to be connected to the functional park provided in the second unit 130, shown as a block diagram in FIG. 24. The functional park shown in this figure is a non-limiting example of the different parts comprised in a control assembly according to the invention.

MCU 52

A micro controller unit (MCU) 152 is provided as a main controller unit of the control assembly 1110 and it thus provided with control software for controlling the operation of the functional part of the control assembly. In a preferred embodiment, this MCU is a Texas Instruments MSP430F149 MCU. Although not shown in the figure, the MCU can be supplemented by additional peripheral circuits, such as a gate array implemented as an application specific integrated circuit (ASIC), acting as an interface to the various functional part.

The MCU 152 receives commands from the energizer 110 via a wireless communication link, see below, and takes decision about actions. The MCU 152 thus supervises all functions in the control assembly 1110.

The MCU stores application specific parameters and calibration data in an external EEPROM (not shown).

The main functionality of the control assembly 1110 is that all operations, such as stimuli, adjustment or measurements are initiated via the energizer 110. Thus, the energizer has two main functions: User interface via RF communication with the control assembly 110 and energy transfer to the control assembly.

The control assembly 110 can be OFF or in Standby when "unconnected". All functions within the control assembly are controlled via the wireless communication link.

The energy transfer function runs in the background as soon as the user has initiated a charge operation. The coupling between the energizer and the receiver coil is displayed by means of a graphical user interface (GUI) on the display of the energizer 110.

If the communication is interrupted under operation, the active function is terminated with a warning message. As soon as correct connection is obtained the last function can be re-activated from the GUI.

Charge Control Unit 154

The MCU 152 is connected to a charge control unit 154, which in turn is connected to the coil 150, which in this embodiment is provided in the first unit 120. The charge control unit comprises an energy storage capacitor 154*a*, from which the normal power supply is taken. In the preferred embodiment, the energy storage capacitor 154*a* has a value of at least 300 Farad with a maximum voltage of 2.3V. The energy storage capacitor is normally connected to the energy transfer coil 150, preventing hazardous voltages to occur at the supply circuits. The voltage from the energy transfer coil 150 is rectified by means of half-wave rectification.

The transferred energy is set by the voltage on the energizer transmit coil 110*a*, see FIG. 5, and the geometric placement relative the energy transfer coil 1110*a* on the control assembly. The leakage inductances make the behavior of a current generator, that is, the voltage across the energy storage capacitor 154*a* will have a very little influence on the current.

The charge function is controlled from the energizer software, which depends on current and voltage readings on the reservoir capacitor.

The applied energy transfer will charge the capacitor up to a limit voltage, which in the preferred embodiment is 2.3V, while the charge current preferably is limited to 2 A by the energizer design. If the energy storage capacitor energy drops below a lower limit voltage, in the preferred embodiment 1.2V, MCU 152 will be notified to terminate any activity and go to STAND-BY mode.

An over voltage protection will disconnect the receiver inductor if the energy storage capacitor voltage reaches 2.35V. All functional parts of the control assembly will still be supplied from the capacitor and a battery charge process will continue.

Thus, the voltage will vary between 1.0 and 2.3V dependent of the charge status. This voltage feeds a switch converter for supplying the MCU including any gate array. It is preferred that the gate array supply may be shut down by the MCU to save energy.

The control assembly shall be functional for 36 hours relying on the capacitor only.

A chargeable battery 154*b* is also provided as part of the charge control unit 154. The capacity of the battery is preferably approximately ten times that of the energy storage capacitor 154*a*. In the preferred embodiment, the battery used is three 1.2 V batteries, such as Varta V500-HT, connected in series. This gives a nominal voltage of 3.6V. The battery management consists of two main activities: Charging and de-charging (transfer energy to the reservoir capacitor. Normally the battery is unused and energy is supplied from the capacitor.

A battery charging functionality is implemented in hardware with supervision and control from the MCU 52. The chargeable battery is charged from the energy storage capacitor 154*a* when the voltage across the energy storage capacitor exceeds 1.9V. This limit will prevent the battery charger from emptying the capacitor energy When the voltage across the energy storage capacitor is less than 1.3V, the battery will charge the energy storage capacitor a constant current by means of a step-down converter (not shown). The charge current is in the preferred embodiment 350 mA with dv/dt detection.

Temperature supervision will turn off any charge operation if the battery temperature increases more than 0.7 degrees per min.

The energy transfer is controlled from the software in the computer 112. The MCU 52 will read the voltage and current on the energy storage capacitor 154*a*. The values are then on command transmitted to the computer 112, which controls the energizer. If the energy storage capacitor 154*a* has a 300 F capacitance and the charge current is normally well below 2 A, the voltage changes will be very slow-minutes for a 0.1V increase. This slow behavior makes an ordinary PI-regulator superfluous. The preferred embodiment is an on/off regulator with a 100 mV hysteresis gap.

At the very startup when there may be no energy in the capacitor. A special bypass power will turn on the MCU/transceiver. Thus the feedback communication system will be active almost immediately when the energizer coil is applied.

Power Modes

The control assembly 1110 can be in four different power modes, namely:

OFF: All circuit are turned off. The transceiver 156 is powered from battery 54*b*, but in sleep mode.

WAKE-UP: The power is fee from the energy transfer coil 150, unconditionally of the status of the capacitor 154*a* or the battery 154*b*. This makes the control assembly to respond immediately when the energizer is applied.

STAND-BY: MCU active but no stimuli, sensor or motor voltage active.

ACTIVE: The MCU in operation. Motor/Sensors/Stimuli etc. active

The mode is controlled by the software in the MCU.

Transceiver 156

The MCU 152 communicates with the energizer by means of the antenna 1110*b*, see FIG. 22, which is electrically connected to a transceiver 156 in the control assembly 1110. The transceiver 156 is in turn connected to the MCU 152. The transceiver 156 can be any suitable transceiver circuit and is in the described embodiment a circuit marked under the name ZL70101 by Zarlink Semiconductor Inc. This provides RF communication using the MICS standard. The transceiver preferably uses a serial peripheral interface (SPI) to communicate with the MCU and is specified for 2.1-3.6V supply. The transceiver needs to be under continuous power but have a low power mode with very low quiescent current where it can be woken up by using either by toggling a wakeup input or alternatively by MICS band or 2.4 GHz radio signals.

Antenna 1110*b*

In the preferred embodiment, the antenna 1110*b* is adapted to support MICS telemetry that operates in the dedicated 402-405 MHz band. The most probable implementation of the transceiver 156 will use a system that can be implemented using also a secondary 2.4 GHz ISM band for wake up purposes, which will then also require attention to safeguard antenna functionality also at these frequencies. The wake up antenna is assumed to be identical to the MICS antenna since alternate solutions would require separate hermetic feed through connections that adds considerable costs. The 2.4 GHz aspect of the antenna is an electrically large antenna that works well with most MICS antenna implementations.

Temperature Sensor(s) 158

One temperature sensor will be use for sensing the temperature of the battery and one sensing the encapsulation. It is also possible to connect one or more external temperature sensors. The sensor accuracy is typically +/−0.5 degrees between −30-+70 degrees and better than +/−0.25 degrees between 20-45 degrees.

Pressure Sensors(s) 160

One or more pressure sensors 160 are connected to an A/D input of the MCU 52. The pressure sensors preferably have a sensing range of 0-2 bars. The sensors can be of the SMD 3000 series type 3SC-0500-5212 from Merit Sensor Systems.

Motor Controller(s) 162

One or more motors can be connected to the control assembly 1110. The operation of these motors are controlled by means of a respective motor controller. In a preferred embodiment, this motor controller consists of 5 H-bridge with current measurement and rotation sensing. The control options are forward, backward, or break. The control is either ON or OFF, i.e., no speed control is implemented. Alternatively, speed control can be implemented, such as by means of a pulse width modulated (PWM) signal.

In order to conserve power, a select signal to each motors current feedback needs to be activated before any measurements can be done.

The current through the motor is measured in order to differentiate four states:

Normal running operation

Motor stall

Motor short-circuit/open circuit

Slipping of magnetic clutch

Different mechanics and motors will have different thresholds for the states. This will be evaluated by software.

The rotation of the motors will be monitored either by an internal encoder in the motor or by external sensors/encoders. The sensing of the movement can be done with a low power Hall element, for example Allegro A139X series, in combination with a comparator that sets the sensitivity or by optical encoders depending on the mechanics. There are two sensors for each motor to be able to determine both speed and direction. End switches can optionally be provided.

Depending on the mechanics and the motors different rotation sensing methods can be used. Exact trip points and hysteresis are application dependent. It should be noted that the mentioned sensors are merely examples and that more types can be added.

Sensing on outgoing axle can be used when there is no encoder on the motor. The rotation sensing can be done with two Hall-effect sensors, such as A1391SE sensors from Allegro Micro Systems, Inc. By using two sensors per motor both direction and speed can be determined. The phase between the detectors shall be 90 degrees, which is set by the mechanical mounting of the devices.

Alternatively, a reflex detector can be used for rotation sensing.

In yet an alternative embodiment, an integrated encoder in the motor can be used for rotation determination.

Stimuli Generator(s) 164

The control assembly can be adapted to control the operation of an implanted medical device in the form of one or more electrodes used to electrically stimulate an organ in the patient' body, such as the corpora cavernosa or crura or the prolongations thereof of a male patient's penile tissue, the colon, rectum, or anus or the prolongation thereof, the urine bladder, the urethra or the prolongation thereof, or any other bodily lumen which requires electrical stimulation under control of the patient or a doctor.

The stimuli generators 164 are designed around a high speed, high current output operational amplifiers, such as the AD825 from Analog Devices, Inc. Each output has a dc current blocking capacitor. A DC servo prevents the capacitor to charge due to offset current errors In one embodiment, the implanted medical device contains 4+4 electrodes to which a constant current pulse generator is connected. The current generator can be connected to two or several electrodes simultaneously.

The current pulses always consist of one positive current pulse and one negative current pulse in any order. The stimuli pulses are configurable regarding current amplitude; pulse widths, number of pulses in a pulse train and pulse frequency. The control assembly 1110 ensures that the pulses are charged balanced.

The software of the computer 112 is adapted to write configuration parameters to the control assembly 1110 and to start and stop stimulation with those parameters. The stimulation can "move" between different electrodes to e.g. create an artificial peristalsis.

In a preferred embodiment, the stimuli amplitude is be up to 20 mA with +/−14V available.

Capacitor Measurement Device 166

One or more capacitance measuring inputs are provided for determination of a physical or mechanical position. The input has a working range of 5-100 pF.

Motion Sensor 168

The motion sensor is a piezo polymer strip that generates a charge/voltage during movement of an intestine. Each motion sensor is adjusted depending of the application in order to apply an appropriate gain.

The first unit 120 could comprises an injection port 170 adapted to receive an injection needle. The injection port comprises a reservoir with a silicone septum. Fluid is added to or removed from the interior reservoir of the first unit 120 by inserting a Huber needle percutaneously into the septum. Although the septum is made of silicone, the means of the injection port for receiving a needle includes any structure configured to self seal after puncture with a non-coring needle.

Different systems comprising an assembly 1110 will now be described.

FIG. 25 illustrates a system for treating a disease comprising an implanted medical device 100 placed in the abdomen of a patient. An implanted energy-transforming device 1002, corresponding to the control assembly 1110, is adapted to supply energy consuming components of the apparatus with energy via a power supply line 1003. An external energy-transmission device 1004, corresponding to the energizer 110, for non-invasively energizing the implanted medical device 100 transmit energy by at least one wireless energy signal. The implanted energy-transforming device 1002 transforms energy from the wireless energy signal into electric energy which is supplied via the power supply line 1003.

The wireless energy signal may include a wave signal selected from the following: a sound wave signal, an ultrasound wave signal, an electromagnetic wave signal, an infrared light signal, a visible light signal, an ultra violet light signal, a laser light signal, a micro wave signal, a radio wave signal, an x-ray radiation signal and a gamma radiation signal. Alternatively, the wireless energy signal may include an electric or magnetic field, or a combined electric and magnetic field.

The wireless energy-transmission device 1004 may transmit a carrier signal for carrying the wireless energy signal. Such a carrier signal may include digital, analogue or a combination of digital and analogue signals. In this case, the wireless energy signal includes an analogue or a digital signal, or a combination of an analogue and digital signal.

Generally speaking, the energy-transforming device 1002 is provided for transforming wireless energy of a first form transmitted by the energy-transmission device 1004 into energy of a second form, which typically is different from the energy of the first form. The implanted medical device 100 is operable in response to the energy of the second form. The energy-transforming device 1002 may directly power the apparatus with the second form energy, as the energy-transforming device 1002 transforms the first form energy transmitted by the energy-transmission device 1004 into the second form energy. The system may further include an implantable accumulator, wherein the second form energy is used at least partly to charge the accumulator.

Alternatively, the wireless energy transmitted by the energy-transmission device 1004 may be used to directly power the apparatus, as the wireless energy is being transmitted by the energy-transmission device 1004. Where the system comprises an operation device for operating the apparatus, as will be described below, the wireless energy transmitted by the energy-transmission device 1004 may be used to directly power the operation device to create kinetic energy for the operation of the apparatus.

The wireless energy of the first form may comprise sound waves and the energy-transforming device 1002 may include a piezo-electric element for transforming the sound waves into electric energy. The energy of the second form may comprise electric energy in the form of a direct current or pulsating direct current, or a combination of a direct current and pulsating direct current, or an alternating current or a combination of a direct and alternating current. Normally, the apparatus comprises electric components that are energized with electrical energy. Other implantable electric components of the system may be at least one voltage level guard or at least one constant current guard connected with the electric components of the apparatus.

Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

The energy-transmission device may be controlled from outside the patients body to release electromagnetic wireless energy, and the released electromagnetic wireless energy is used for operating the apparatus. Alternatively, the energy-transmission device is controlled from outside the patients body to release non-magnetic wireless energy, and the released non-magnetic wireless energy is used for operating the apparatus.

The external energy-transmission device 1004 also includes a wireless remote control having an external signal transmitter for transmitting a wireless control signal for non-invasively controlling the apparatus. The control signal is received by an implanted signal receiver which may be incorporated in the implanted energy-transforming device 1002 or be separate there from.

The wireless control signal may include a frequency, amplitude, or phase modulated signal or a combination thereof. Alternatively, the wireless control signal includes an analogue or a digital signal, or a combination of an analogue and digital signal. Alternatively, the wireless control signal comprises an electric or magnetic field, or a combined electric and magnetic field.

The wireless remote control may transmit a carrier signal for carrying the wireless control signal. Such a carrier signal may include digital, analogue or a combination of digital and analogue signals. Where the control signal includes an analogue or a digital signal, or a combination of an analogue and digital signal, the wireless remote control preferably transmit an electromagnetic carrier wave signal for carrying the digital or analogue control signals.

FIG. 26 illustrates the system of FIG. 25 in the form of a more generalized block diagram showing the implanted medical device 100, the energy-transforming device 1002 powering the implanted medical device 100 via power supply line 1003, and the external energy-transmission device 1004, The patients skin 1005, generally shown by a vertical line, separates the interior of the patient to the right of the line from the exterior to the left of the line.

FIG. 27 shows an embodiment of the invention identical to that of FIG. 26, except that a reversing device in the form of an electric switch 1006 operable for example by polarized energy also is implanted in the patient for reversing the implanted medical device 100. When the switch is operated by polarized energy the wireless remote control of the external energy-transmission device 1004 transmit a wireless signal that carries polarized energy and the implanted energy-transforming device 1002 transforms the wireless polarized energy into a polarized current for operating the electric switch 1006. When the polarity of the current is shifted by the implanted energy-transforming device 1002 the electric switch 1006 reverses the function performed by the implanted medical device 100.

FIG. 28 shows an embodiment of the invention identical to that of FIG. 26, except that an operation device 1007 implanted in the patient for operating the implanted medical device 100 is provided between the implanted energy-transforming device 1002 and the implanted medical device 100. This operation device can be in the form of a motor 1007, such as an electric servomotor. The motor 1007 is powered with energy from the implanted energy-transforming device 1002, as the remote control of the external energy-transmission device 1004 transmit a wireless signal to the receiver of the implanted energy-transforming device 1002.

FIG. 29 shows an embodiment of the invention identical to that of FIG. 26, except that it also comprises an operation device is in the form of an assembly 1008 including a motor/pump unit 1009 and a fluid reservoir 1010 is implanted in the patient. In this case the implanted medical device 100 is hydraulically operated, i.e. hydraulic fluid is pumped by the motor/pump unit 1009 from the fluid reservoir 1010 through a conduit 1011 to the implanted medical device 100 to operate the apparatus, and hydraulic fluid is pumped by the motor/pump unit 1009 back from the implanted medical device 100 to the fluid reservoir 1010 to return the apparatus to a starting position. The implanted energy-transforming device 1002 transforms wireless energy into a current, for example a polarized current, for powering the motor/pump unit 1009 via an electric power supply line 1012.

Instead of a hydraulically operated apparatus 1110, it is also envisaged that the operation device comprises a pneumatic operation device. In this case, the hydraulic fluid can be pressurized air to be used for regulation and the fluid reservoir is replaced by an air chamber.

In all of these embodiments the energy-transforming device 1002 may include a rechargeable accumulator like a battery or a capacitor to be charged by the wireless energy and supplies energy for any energy consuming part of the system.

As an alternative, the wireless remote control described above may be replaced by manual control of any implanted part to make contact with by the patients hand most likely indirect, for example a press button placed under the skin.

Figure 30:
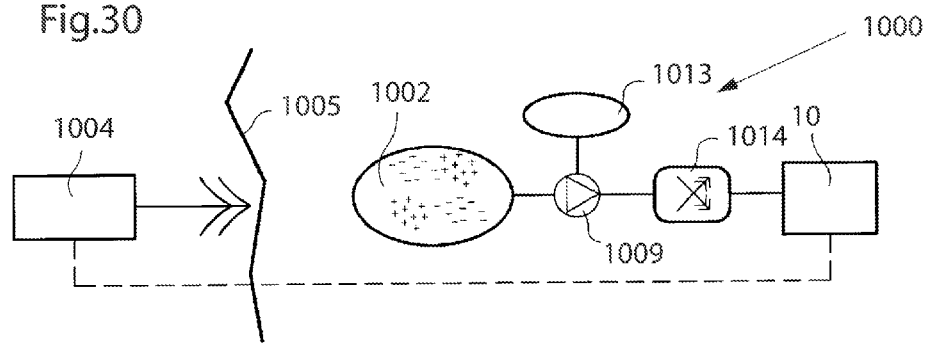

FIG. 30 shows an embodiment of the invention comprising the external energy-transmission device 1004 with it wireless remote control, the apparatus 1110, in this case hydraulically operated, and the implanted energy-transforming device 1002, and further comprising a hydraulic fluid reservoir 1013, a motor/pump unit 1009 and an reversing device in the form of a hydraulic valve shilling device 1014, all implanted in the patient. Of course the hydraulic operation could easily be performed by just changing the pumping direction and the hydraulic valve may therefore be omitted. The remote control may be a device separated from the external energy-transmission device or included in the same. The motor of the motor/pump unit 1009 is an electric motor. In response to a control signal from the wireless remote control of the external energy-transmission device 1004, the implanted energy-transforming device 1002 powers the motor/pump unit 1009 with energy from the energy carried by the control signal, whereby the motor/pump unit 1009 distributes hydraulic fluid between the hydraulic fluid reservoir 1013 and the apparatus 10. The remote control of the external energy-transmission device 1004 controls the hydraulic valve shilling device 1014 to shift the hydraulic fluid flow direction between one direction in which the fluid is pumped by the motor/pump unit 1009 from the hydraulic fluid reservoir 1013 to the implanted medical device 100 to operate the apparatus, and another opposite direction in which the fluid is pumped by the motor/pump unit 1009 back from the implanted medical device 100 to the hydraulic fluid reservoir 1013 to return the apparatus to a starting position.

Figure 31:
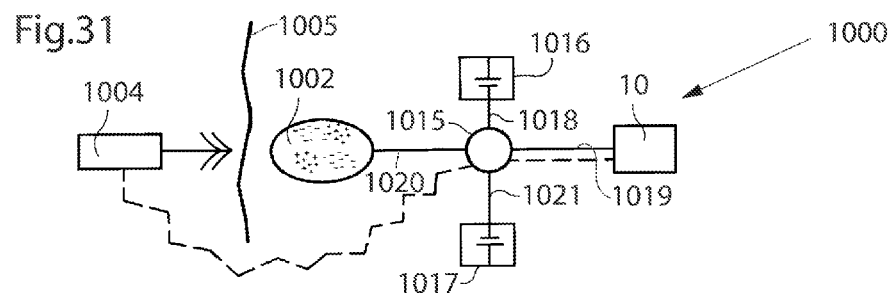

FIG. 31 shows an embodiment of the invention comprising the external energy-transmission device 1004 with its wireless remote control, the apparatus 1110, the implanted energy-transforming device 1002, an implanted internal control unit 1015 controlled by the wireless remote control of the external energy-transmission device 1004, an implanted accumulator 1016 and an implanted capacitor 1017. The internal control unit 1015 arranges storage of electric energy received from the implanted energy-transforming device 1002 in the accumulator 1016, which supplies energy to the apparatus 1110. In response to a control signal from the wireless remote control of the external energy-transmission device 1004, the internal control unit 1015 either releases electric energy from the accumulator 1016 and transfers the released energy via power lines 1018 and 1019, or directly transfers electric energy from the implanted energy-transforming device 1002 via a power line 1020, the capacitor 1017, which stabilizes the electric current, a power line 1021 and the power line 1019, for the operation of the apparatus 1110.

The internal control unit is preferably programmable from outside the patient's body. In a preferred embodiment, the internal control unit is programmed to regulate the implanted medical device 100 according to a pre-programmed time-schedule or to input from any sensor sensing any possible physical parameter of the patient or any functional parameter of the system.

In accordance with an alternative, the capacitor 1017 in the embodiment of FIG. 31 may be omitted. In accordance with another alternative, the accumulator 1016 in this embodiment may be omitted.

Figure 32:
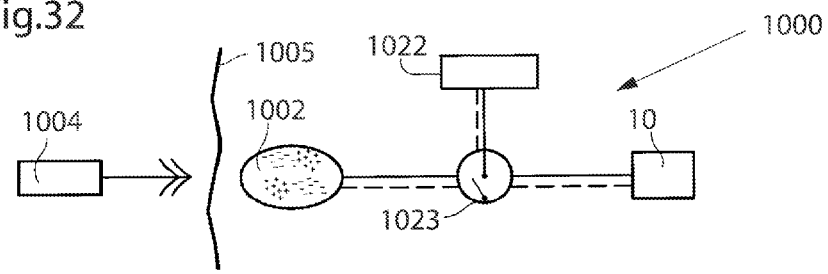

FIG. 32 shows an embodiment of the invention identical to that of FIG. 16, except that a battery 1022 for supplying energy for the operation of the implanted medical device 100 and an electric switch 1023 for switching the operation of the implanted medical device 100 also are implanted in the patient. The electric switch 1023 may be controlled by the remote control and may also be operated by the energy supplied by the implanted energy-transforming device 1002 to switch from an off mode, in which the battery 1022 is not in use, to an on mode, in which the battery 1022 supplies energy for the operation of the apparatus 1110.

Figure 33:
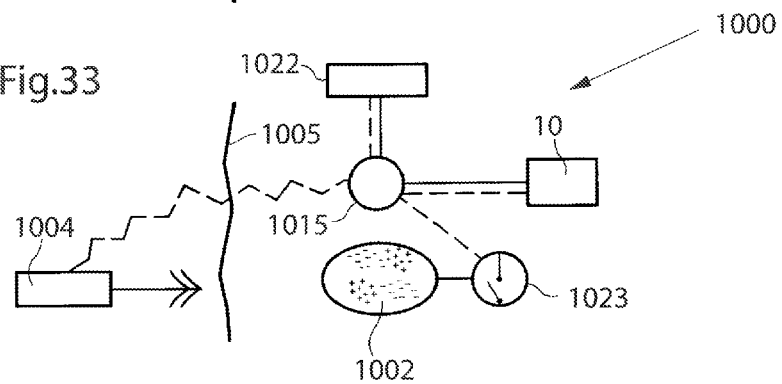

FIG. 33 shows an embodiment of the invention identical to that of FIG. 32, except that an internal control unit 1015 controllable by the wireless remote control of the external energy-transmission device 1004 also is implanted in the patient. In this case, the electric switch 1023 is operated by the energy supplied by the implanted energy-transforming device 1002 to switch from an off mode, in which the wireless remote control is prevented from controlling the internal control unit 1015 and the battery is not in use, to a standby mode, in which the remote control is permitted to control the internal control unit 1015 to release electric energy from the battery 1022 for the operation of the apparatus 1110.

Figure 34:
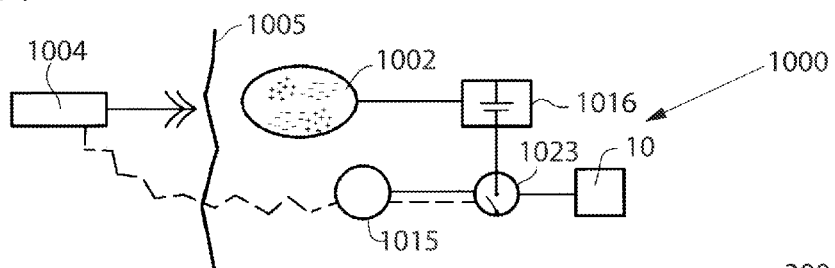

FIG. 34 shows an embodiment of the invention identical to that of FIG. 18, except that an accumulator 1016 is substituted for the battery 1022 and the implanted components are interconnected differently. In this case, the accumulator 1016 stores energy from the implanted energy-transforming device 1002. In response to a control signal from the wireless remote control of the external energy-transmission device 1004, the internal control unit 1015 controls the electric switch 1023 to switch from an off mode, in which the accumulator 1016 is not in use, to an on mode, in which the accumulator 1016 supplies energy for the operation of the apparatus 10. The accumulator may be combined with or replaced by a capacitor.

Figure 35:
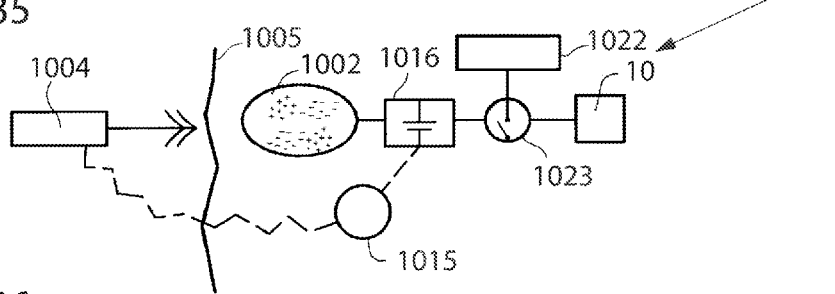

FIG. 35 shows an embodiment of the invention identical to that of FIG. 34, except that a battery 1022 also is implanted in the patient and the implanted components are interconnected differently. In response to a control signal from the wireless remote control of the external energy-transmission device 1004, the internal control unit 1015 controls the accumulator 1016 to deliver energy for operating the electric switch 1023 to switch from an off mode, in which the battery 1022 is not in use, to an on mode, in which the battery 1022 supplies electric energy for the operation of the apparatus 1110.

Alternatively, the electric switch 1023 may be operated by energy supplied by the accumulator 1016 to switch from an off mode, in which the wireless remote control is prevented from controlling the battery 1022 to supply electric energy and is not in use, to a standby mode, in which the wireless remote control is permitted to control the battery 1022 to supply electric energy for the operation of the apparatus 1110.

It should be understood that the switch 1023 and all other switches in this application should be interpreted in its broadest embodiment. This means a transistor, MCU, MCPU, ASIC, FPGA or a DA converter or any other electronic component or circuit that may switch the power on and off. Preferably the switch is controlled from outside the body, or alternatively by an implanted internal control unit.

Figure 36:
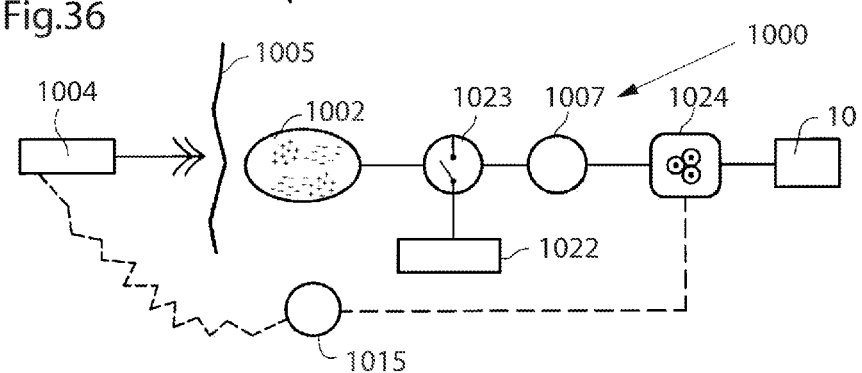

FIG. 36 shows an embodiment of the invention identical to that of FIG. 32, except that a motor 1007, a mechanical reversing device in the form of a gear box 1024, and an internal control unit 1015 for controlling the gear box 1024 also are implanted in the patient. The internal control unit 1015 controls the gear box 1024 to reverse the function performed by the implanted medical device 100 (mechanically operated). Even simpler is to switch the direction of the motor electronically. The gear box interpreted in it broadest embodiment may stand for a servo arrangement saving force for the operation device in favor of longer stroke to act.

Figure 37:
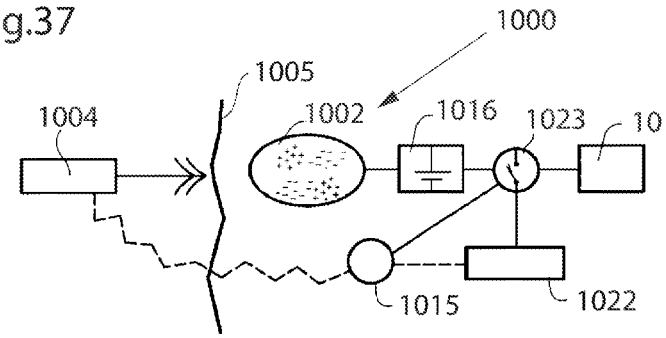

FIG. 37 shows an embodiment of the invention identical to that of FIG. 36 except that the implanted component are interconnected differently. Thus, in this case the internal control unit 1015 is powered by the battery 1022 when the accumulator 1016, suitably a capacitor, activates the electric switch 1023 to switch to an on mode. When the electric switch 1023 is inks on mode the internal control unit 1015 is permitted to control the battery 1022 to supply, or not supply, energy for the operation of the apparatus 1110.

Figure 38:
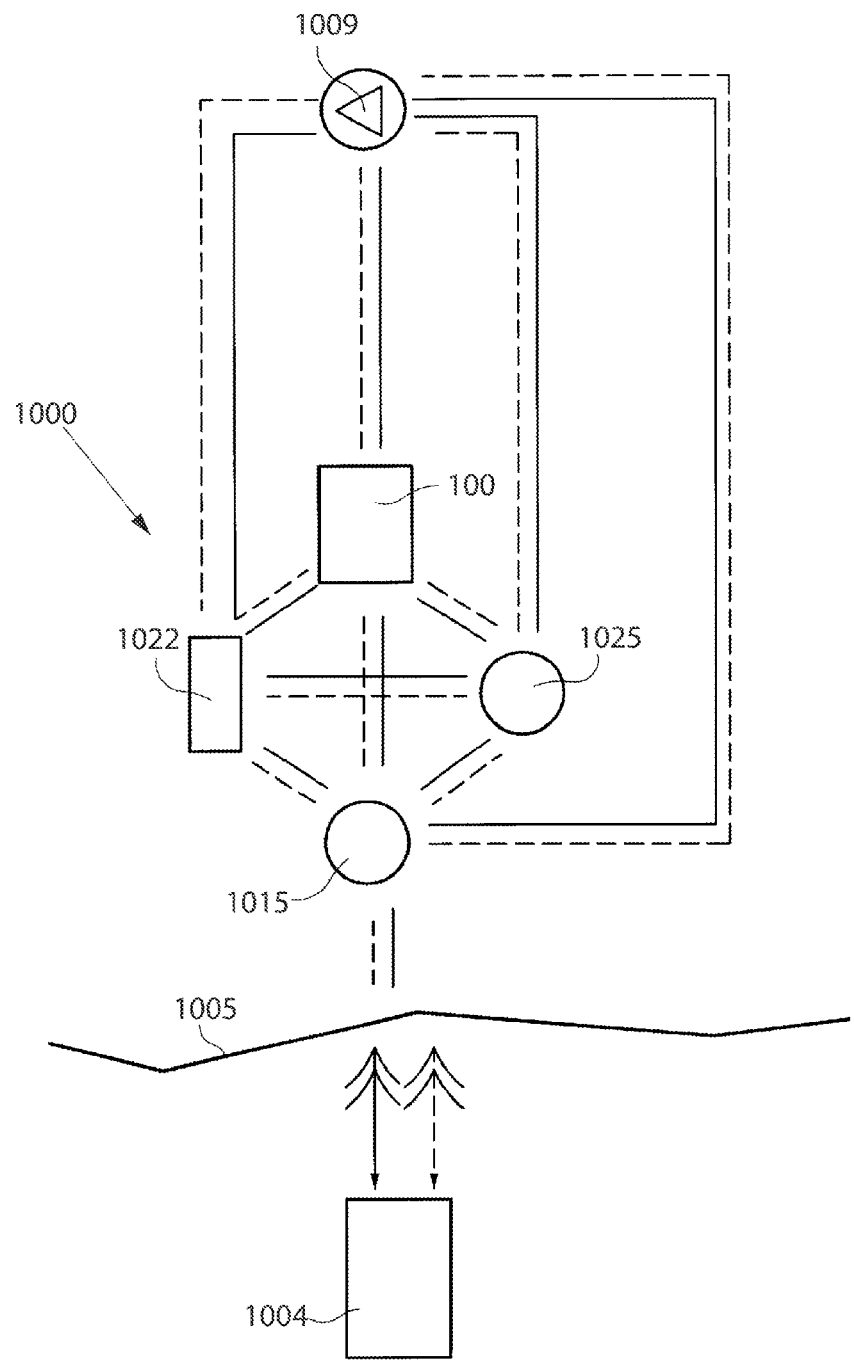

FIG. 38 schematically shows conceivable combinations of implanted component of the apparatus for achieving various communication options. Basically, there are the apparatus 1110, the internal control unit 1015, motor or pump unit 1009, and the external energy-transmission device 1004 including the external wireless remote control. As already described above the wireless remote control transmit a control signal which is received by the internal control unit 1015, which in turn controls the various implanted component of the apparatus.

A feedback device, preferably comprising a sensor or measuring device 1025, may be implanted in the patient for sensing a physical parameter of the patient. The physical parameter may be at least one selected from the group consisting of pressure, volume, diameter, stretching, elongation, extension, movement, bending, elasticity, muscle contraction, nerve impulse, body temperature, blood pressure, blood flow, heartbeats and breathing. The sensor may sense any of the above physical parameters. For example, the sensor may be a pressure or motility sensor. Alternatively, the sensor 1025 may be arranged to sense a functional parameter. The functional parameter may be correlated to the transfer of energy for charging an implanted energy source and may further include at least one selected from the group of parameters consisting of; electricity, any electrical parameter, pressure, volume, diameter, stretc, elongation, extension, movement, bending, elasticity, temperature and flow.

The feedback may be sent to the internal control unit or out to an external control unit preferably via the internal control unit. Feedback may be sent out from the body via the energy transfer system or a separate communication system with receiver and transmitters.

The internal control unit 1015, or alternatively the external wireless remote control of the external energy-transmission device 1004, may control the implanted medical device 100 in response to signals from the sensor 1025. A transceiver may be combined with the sensor 1025 for sending information on the sensed physical parameter to the external wireless remote control. The wireless remote control may comprise a signal transmitter or transceiver and the internal control unit 1015 may comprise a signal receiver or transceiver. Alternatively, the wireless remote control may comprise a signal receiver or transceiver and the internal control unit 1015 may comprise a signal transmitter or transceiver. The above transceivers, transmitters and receivers may be used for sending information or data related to the implanted medical device 100 from inside the patients body to the outside thereof.

Where the motor/pump unit 1009 and battery 1022 for powering the motor/pump unit 1009 are implanted, information related to the charging of the battery 1022 may be fed back. To be more precise, when charging a battery or accumulator with energy feed back information related to said charging process is sent and the energy supply is changed accordingly.

Figure 39:
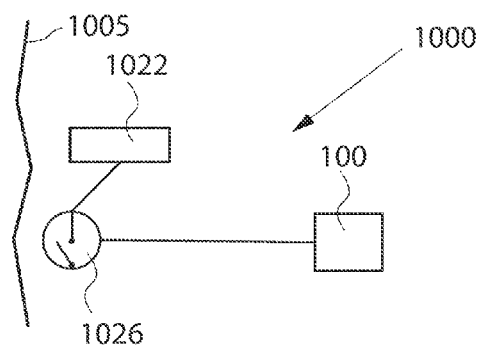

FIG. 39 shows an alternative embodiment wherein the implanted medical device 100 is regulated from outside the patients body. The system 1000 comprises a battery 1022 connected to the implanted medical device 100 via a subcutaneous electric switch 1026. Thus, the regulation of the implanted medical device 100 is performed non-invasively by manually pressing the subcutaneous switch, whereby the operation of the implanted medical device 100 is switched on and off. It will be appreciated that the shown embodiment is a simplification and that additional component, such as an internal control unit or any other part disclosed in the present application can be added to the system. Two subcutaneous switches may also be used. In the preferred embodiment one implanted switch sends information to the internal control unit to perform a certain predetermined performance and when the patient press the switch again the performance is reversed.

Figure 40:
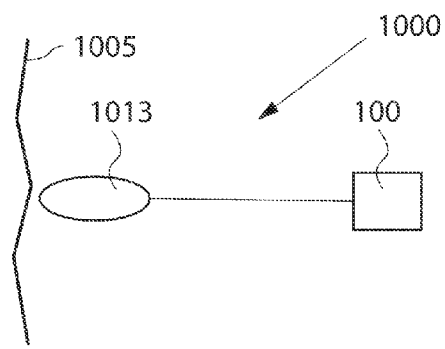

FIG. 40 shows an alternative embodiment, wherein the system 1000 comprises a hydraulic fluid reservoir 1013 hydraulically connected to the apparatus. Non-invasive regulation is performed by manually pressing the hydraulic reservoir connected to the apparatus.

The system may include an external data communicator and an implantable internal data communicator communicating with the external data communicator. The internal communicator feeds data related to the apparatus or the patient to the external data communicator and/or the external data communicator feeds data to the internal data communicator.

Figure 41:
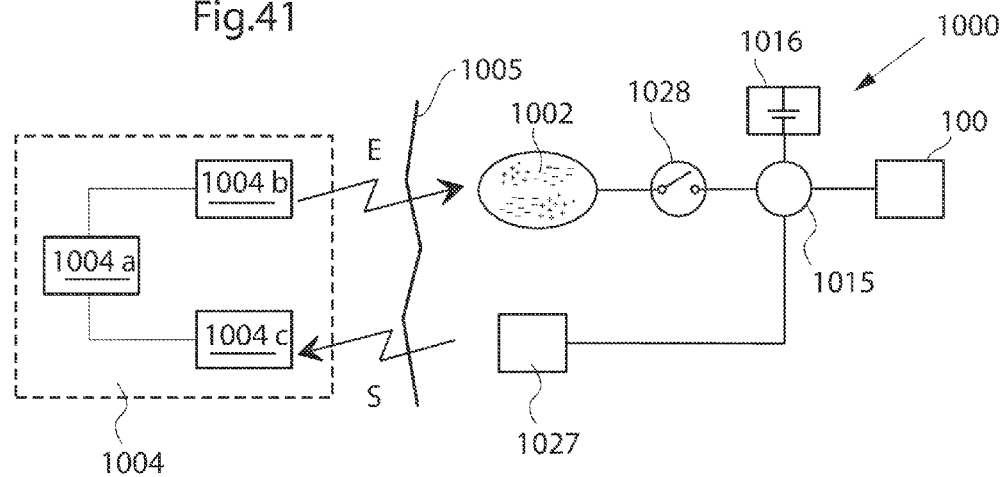

FIG. 41 schematically illustrates an arrangement of the system that is capable of sending information from inside the patients body to the outside thereof to give feedback information related to at least one functional parameter of the apparatus or system, or related to a physical parameter of the patient, in order to supply an accurate amount of energy to an implanted internal energy receiver 1002 connected to implanted energy consuming component of the apparatus 1110. Such an energy receiver 1002 may include an energy source and/or an energy-transforming device. Briefly described, wireless energy is transmitted from an external energy source 1004a located outside the patient and is received by the internal energy receiver 1002 located inside the patient. The internal energy receiver is adapted to directly or indirectly supply received energy to the energy consuming component of the implanted medical device 100 via a switch 1026. An energy balance is determined between the energy received by the internal energy receiver 1002 and the energy used for the apparatus 1110, and the transmission of wireless energy is then controlled based on the determined energy balance. The energy balance thus provides an accurate indication of the correct amount of energy needed, which is sufficient to operate the implanted medical device 100 properly, but without causing undue temperature rise.

In FIG. 41 the patients skin is indicated by a vertical line 1005. Here, the energy receiver comprises an energy-transforming device 1002 located inside the patient, preferably just beneath the patient's skin 1005. Generally speaking, the implanted energy-transforming device 1002 may be placed in the abdomen, thorax, muscle fascia (e.g. in the abdominal wall), subcutaneously, or at any other suitable location. The implanted energy-transforming device 1002 is adapted to receive wireless energy E transmitted from the external energy-source 1004a provided in an external energy-transmission device 1004 located outside the patients skin 1005 in the vicinity of the implanted energy-transforming device 1002.

As is well known in the art, the wireless energy E may generally be transferred by means of any suitable Transcutaneous Energy Munster (TET) device, such as a device including a primary coil arranged in the external energy source 1004a and an adjacent secondary coil arranged in the implanted energy-transforming device 1002. When an electric current is fed through the primary coil, energy in the form of a voltage is induced in the secondary coil which can be used to power the implanted energy consuming component of the apparatus, e.g. after storing the incoming energy in an implanted energy source, such as a rechargeable battery or a capacitor. However, the present invention is generally not limited to any particular energy transfer technique, TET devices or energy sources, and any kind of wireless energy may be used.

The amount of energy received by the implanted energy receiver may be compared with the energy used by the implanted component of the apparatus. The term "energy used" is then understood to include also energy stored by implanted component of the apparatus. A control device includes an external control unit 1004b that controls the external energy source 1004a based on the determined energy balance to regulate the amount of transferred energy. In order to transfer the correct amount of energy, the energy balance and the required amount of energy is determined by means of a determination device including an implanted internal control unit 1015 connected between the switch 1026 and the apparatus 1110. The internal control unit 1015 may thus be arranged to receive various measurements obtained by suitable sensors or the like, not shown, measuring certain characteristics of the apparatus 1110, somehow reflecting the required amount of energy needed for proper operation of the apparatus 1110. Moreover, the current condition of the patient may also be detected by means of suitable measuring devices or sensors, in order to provide parameters reflecting the patient's condition. Hence, such characteristics and/or parameters may be related to the current state of the apparatus 1110, such as power consumption, operational mode and temperature, as well as the patients condition reflected by parameters such as; body temperature, blood pressure, heartbeats and breathing. Other kinds of physical parameters of the patient and functional parameters of the device are described elsewhere.

Furthermore, an energy source in the form of an accumulator 1016 may optionally be connected to the implanted energy-transforming device 1002 via the control unit 1015 for accumulating received energy for later use by the apparatus 1110. Alternatively or additionally, characteristics of such an accumulator, also reflecting the required amount of energy, may be measured as well. The accumulator may be replaced by a rechargeable battery, and the measured characteristics may be related to the current state of the battery, any electrical parameter such as energy consumption voltage, temperature, etc. In order to provide sufficient voltage and current to the apparatus 1110, and also to avoid excessive heating, it is clearly understood that the battery should be charged optimally by receiving a correct amount of energy from the implanted energy-transforming device 1002, i.e. not too little or too much. The accumulator may also be a capacitor with corresponding characteristics.

For example, battery characteristics may be measured on a regular basis to determine the current state of the battery, which then may be stored as state information in a suitable storage means in the internal control unit 1015. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 1015 of the determination device is adapted to determine the energy balance and/or the currently required amount of energy, (either energy per time unit or accumulated energy) based on measurements made by the above-mentioned sensors or measuring devices of the apparatus 1110, or the patient, or an implanted energy source if used, or any combination thereof. The internal control unit 1015 is further connected to an internal signal transmitter 1027, arranged to transmit a control signal reflecting the determined required amount of energy, to an external signal receiver 1004c connected to the external control unit 1004b. The amount of energy transmitted from the external energy source 1004a may then be regulated in response to the received control signal.

Alternatively, the determination device may include the external control unit 1004b. In this alternative, sensor measurements can be transmitted directly to the external control unit 1004b wherein the energy balance and/or the currently required amount of energy can be determined by the external control unit 1004b, thus integrating the above-described function of the internal control unit 1015 in the external control unit 1004b. In that case, the internal control unit 1015 can be omitted and the sensor measurements are supplied directly to the internal signal transmitter 1027 which sends the measurements over to the external signal receiver 1004c and the external control unit 1004b. The energy balance and the currently required amount of energy can then be determined by the external control unit 1004b based on those sensor measurements.

Hence, the present solution according to the arrangement of FIG. 41 employs the feed back of information indicating the required energy, which is more efficient than previous solutions because it is based on the actual use of energy that is compared to the received energy, e.g. with respect to the amount of energy, the energy difference, or the energy receiving rate as compared to the energy rate used by implanted energy consuming component of the apparatus. The apparatus may use the received energy either for consuming or for storing the energy in an implanted energy source or the like. The different parameters discussed above would thus be used if relevant and needed and then as a tool for determining the actual energy balance. However, such parameters may also be needed per se for any actions taken internally to specifically operate the apparatus.

The internal signal transmitter 1027 and the external signal receiver 1004c may be implemented as separate unit using suitable signal transfer means, such as radio, IR (Infrared) or ultrasonic signals. Alternatively, the internal signal transmitter 1027 and the external signal receiver 1004c may be integrated in the implanted energy-transforming device 1002 and the external energy source 1004a, respectively, so as to convey control signals in a reverse direction relative to the energy transfer, basically using the same transmission technique. The control signals may be modulated with respect to frequency, phase or amplitude.

Thus, the feedback information may be transferred either by a separate communication system including receivers and transmitters or may be integrated in the energy system. In accordance with the present invention, such an integrated information feedback and energy system comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmit wireless energy which is received by the first coil of the energy receiver. This system further comprises a power switch for switching the connection of the internal first coil to the first electronic circuit on and off, such that feedback information related to the charging of the first coil is received by the external energy transmitter in the form of an impedance variation in the load of the external second coil, when the power switch switches the connection of the internal first coil to the first electronic circuit on and off. In implementing this system in the arrangement of FIG. 41, the switch 1026 is either separate and controlled by the internal control unit 1015, or integrated in the internal control unit 1015. It should be understood that the switch 1026 should be interpreted in it broadest embodiment. This means a transistor, MCU, MCPU, ASIC FPGA or a DA converter or any other electronic component or circuit that may switch the power on and off.

To conclude, the energy supply arrangement illustrated in FIG. 41 may operate basically in the following manner. The energy balance is first determined by the internal control unit 1015 of the determination device. A control signal reflecting the required amount of energy is also created by the internal control unit 1015, and the control signal is transmitted from the internal signal transmitter 1027 to the external signal receiver 1004c. Alternatively, the energy balance can be determined by the external control unit 1004b instead depending on the implementation, as mentioned above. In that case, the control signal may carry measurement result from various sensors. The amount of energy emitted from the external energy source 1004a can then be regulated by the external control unit 1004b, based on the determined energy balance, e.g. in response to the received control signal. This process may be repeated intermittently at certain intervals during ongoing energy transfer, or may be executed on a more or less continuous basis during the energy transfer.

The amount of transferred energy can generally be regulated by adjusting various transmission parameters in the external energy source 1004a, such as voltage, current, amplitude, wave frequency and pulse characteristics.

This system may also be used to obtain information about the coupling factors between the coils in a TET system even to calibrate the system both to find an optimal place for the external coil in relation to the internal coil and to optimize energy transfer. Simply comparing in this case the amount of energy transferred with the amount of energy received. For example if the external coil is moved the coupling factor may vary and correctly displayed movements could cause the external coil to find the optimal place for energy transfer. Preferably, the external coil is adapted to calibrate the amount of transferred energy to achieve the feedback information in the determination device, before the coupling factor is maximized.

This coupling factor information may also be used as a feedback during energy transfer. In such a case, the energy system of the present invention comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a feedback device for communicating out the amount of energy received in the first coil as a feedback information, and wherein the second electronic circuit includes a determination device for receiving the feedback information and for comparing the amount of transferred energy by the second coil with the feedback information related to the amount of energy received in the first coil to obtain the coupling factor between the first and second coils. The energy transmitter may regulate the transmitted energy in response to the obtained coupling factor.

Figure 42:
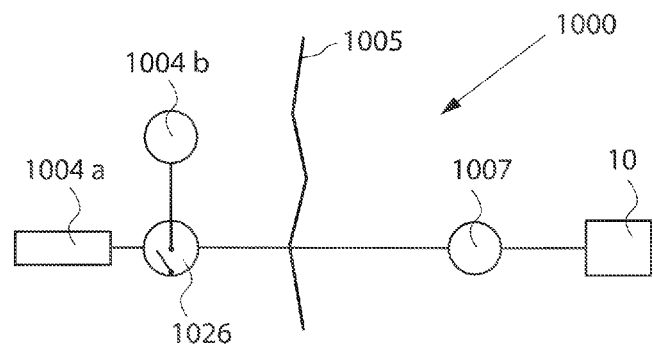

With reference to FIG. 42, although wireless transfer of energy for operating the apparatus has been described above to enable non-invasive operation, it will be appreciated that the apparatus can be operated with wire bound energy as well. Such an example is shown in FIG. 42, wherein an external switch 1026 is interconnected between the external energy source 1004a and an operation device, such as an electric motor 1007 operating the apparatus 1110. An external control unit 1004b controls the operation of the external switch 1026 to effect proper operation of the apparatus 1110.

Figure 43:
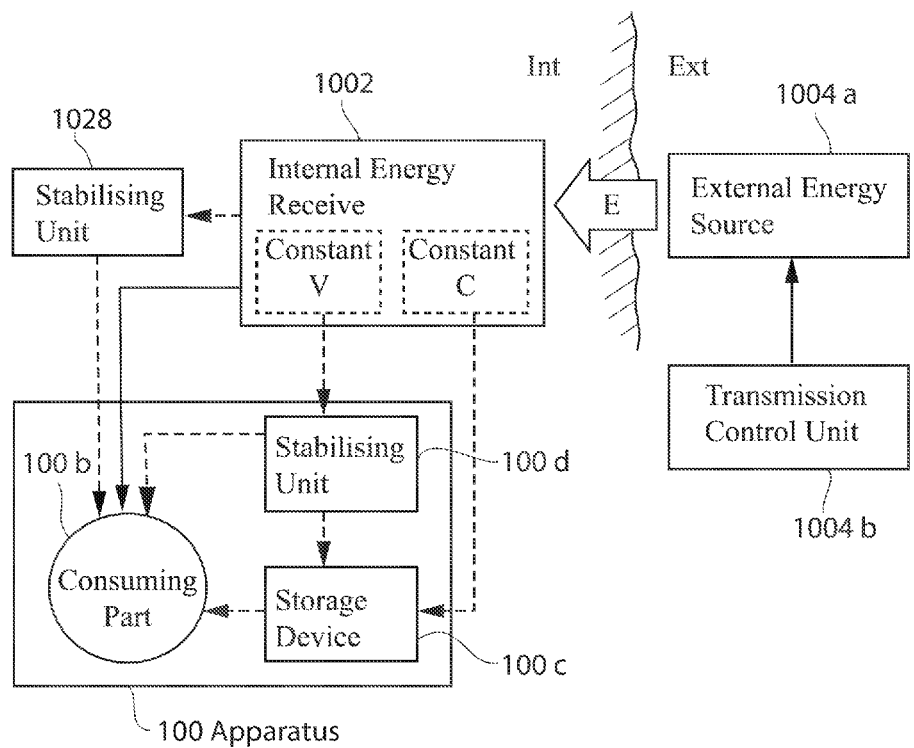
FIG. 43 is a schematic block diagram illustrating an arrangement for supplying an accurate amount of energy used for the operation of the implanted assembly shown in FIG. 1.

FIG. 43 illustrates different embodiments for how received energy can be supplied to and used by the apparatus 1110. Similar to the example of FIG. 41, an internal energy receiver 1002 receives wireless energy E from an external energy source 1004*a* which is controlled by a transmission control unit 1004*b*. The internal energy receiver 1002 may comprise a constant voltage circuit, indicated as a dashed box "constant V" in the figure, for supplying energy at constant voltage to the apparatus 1110. The internal energy receiver 1002 may further comprise a constant current circuit, indicated as a dashed box "constant C" in the figure, for supplying energy at constant current to the apparatus 1110.

The implanted medical device 100 comprises an energy consuming part 100*a*, which may be a motor, pump, restriction device, or any other medical appliance that requires energy for its electrical operation. The implanted medical device 100 may further comprise an energy storage device 100*b* for storing energy supplied from the internal energy receiver 1002. Thus, the supplied energy may be directly consumed by the energy consuming part 100*a*, or stored by the energy storage device 100*b*, or the supplied energy may be partly consumed and partly stored. The implanted medical device 100 may further comprise an energy stabilizing unit 100*c* for stabilizing the energy supplied from the internal energy receiver 1002. Thus, the energy may be supplied in a fluctuating manner such that it may be necessary to stabilize the energy before consumed or stored.

The energy supplied from the internal energy receiver 1002 may further be accumulated and/or stabilized by a separate energy stabilizing unit 1028 located outside the apparatus 1110, before being consumed and/or stored by the apparatus 1110. Alternatively, the energy stabilizing unit 1028 may be integrated in the internal energy receiver 1002. In either case, the energy stabilizing unit 1028 may comprise a constant voltage circuit and/or a constant current circuit.

It should be noted that FIG. 41 and FIG. 43 illustrate some possible but non-limiting implementation options regarding how the various shown functional component and elements can be arranged and connected to each other. However, the skilled person will readily appreciate that many variations and modifications can be made within the scope of the pre sent invention.

Figure 44:
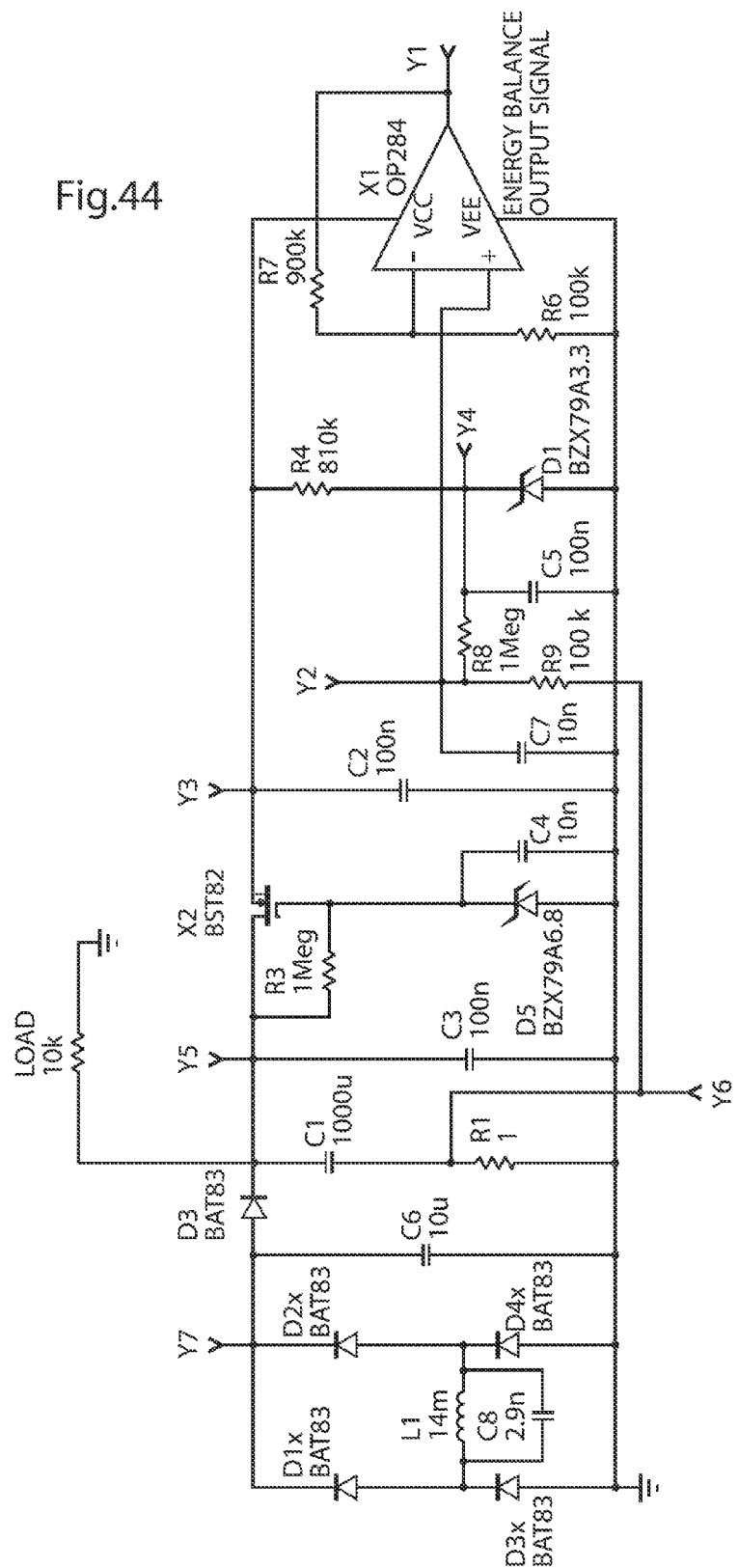
FIG. 44 schematically shows an embodiment of the system, in which the implanted assembly is operated with wire bound energy.

FIG. 44 schematically shows an energy balance measuring circuit of one of the proposed designs of the system for controlling transmission of wireless energy, or energy balance control system. The circuit has an output signal centered on 2.5V and proportionally related to the energy imbalance. The derivative of this signal shows if the value goes up and down and how fast such a change takes place. If the amount of received energy is lower than the energy used by implanted components of the apparatus, more energy is transferred and thus charged into the energy source. The output signal from the circuit is typically feed to an A/D converter and converted into a digital format. The digital information can then be sent to the external energy-transmission device allowing it to adjust the level of the transmitted energy. Another possibility is to have a completely analog system that uses comparators comparing the energy balance level with certain maximum and minimum thresholds sending information to external energy-transmission device if the balance drifts out of the max/min window.

The schematic FIG. 44 shows a circuit implementation for a system that transfers energy to the implanted energy component of the apparatus of the present invention from outside of the patients body using inductive energy transfer. An inductive energy transfer system typically uses an external transmitting coil and an internal receiving coil. The receiving coil, L1, is included in the schematic FIG. 27; the transmitting part of the system are excluded.

The implementation of the general concept of energy balance and the way the information is transmitted to the external energy transmitter can of course be implemented in numerous different ways. The schematic FIG. 44 and the above described method of evaluating and transmitting the information should only be regarded as examples of how to implement the control system.

In FIG. 43 the symbols Y1, Y2, Y3 and so on symbolize test point within the circuit. The component in the diagram and their respective values are values that work in this particular implementation which of course is only one of an infinite number of possible design solutions.

Energy to power the circuit is received by the energy receiving coil L1. Energy to implanted component is transmitted in this particular case at a frequency of 25 kHz. The energy balance output signal is present at test point Y1.

Those skilled in the art will realize that the above various embodiments of the system could be combined in many different ways. For example, the electric switch 1006 of FIG. 27 could be incorporated in any of the embodiments of FIGS. 30-36, the hydraulic valve shilling device 1014 of FIG. 30 could be incorporated in the embodiment of FIG. 29, and the gear box 1024 could be incorporated in the embodiment of FIG. 28. Please observe that the switch simply could mean any electronic circuit or component.

The embodiments described in connection with FIGS. 41, 43 and 44 identify a method and a system for controlling transmission of wireless energy to implanted energy consuming component of an electrically operable apparatus. Such a method and system will be defined in general terms in the following.

A method is thus provided for controlling transmission of wireless energy supplied to implanted energy consuming component of an apparatus as described above. The wireless energy E is transmitted from an external energy source located outside the patient and is received by an internal energy receiver located inside the patient, the internal energy receiver being connected to the implanted energy consuming component of the apparatus for directly or indirectly supplying received energy thereto. An energy balance is determined between the energy received by the internal energy receiver and the energy used for the apparatus. The transmission of wireless energy E from the external energy source is then controlled based on the determined energy balance.

The wireless energy may be transmitted inductively from a primary coil in the external energy source to a secondary coil in the internal energy receiver. A change in the energy balance may be detected to control the transmission of wireless energy based on the detected energy balance change. A difference may also be detected between energy received by the internal energy receiver and energy used for the medical device, to control the transmission of wireless energy based on the detected energy difference.

When controlling the energy transmission, the amount of transmitted wireless energy may be decreased if the detected energy balance change implies that the energy balance is increasing, or vice versa. The decrease/increase of energy transmission may further correspond to a detected change rate.

The amount of transmitted wireless energy may further be decreased if the detected energy difference implies that the received energy is greater than the used energy, or vice versa. The decrease/increase of energy transmission may then correspond to the magnitude of the detected energy difference.

As mentioned above, the energy used for the medical device may be consumed to operate the medical device, and/or stored in at least one energy storage device of the medical device.

When electrical and/or physical parameters of the medical device and/or physical parameters of the patient are determined, the energy may be transmitted for consumption and storage according to a transmission rate per time unit which is determined based on said parameters. The total amount of transmitted energy may also be determined based on said parameters.

When a difference is detected between the total amount of energy received by the internal energy receiver and the total amount of consumed and/or stored energy, and the detected difference is related to the integral over time of at least one measured electrical parameter related to said energy balance, the integral may be determined for a monitored voltage and/or current related to the energy balance.

When the derivative is determined over time of a measured electrical parameter related to the amount of consumed and/or stored energy, the derivative may be determined for a monitored voltage and/or current related to the energy balance.

The transmission of wireless energy from the external energy source may be controlled by applying to the external energy source electrical pulses from a first electric circuit to transmit the wireless energy, the electrical pulses having leading and trailing edges, varying the lengths of first time intervals between successive leading and trailing edges of the electrical pulses and/or the lengths of second time intervals between successive trailing and leading edges of the electrical pulses, and transmitting wireless energy, the transmitted energy generated from the electrical pulses having a varied power, the varying of the power depending on the lengths of the first and/or second time intervals.

In that case, the frequency of the electrical pulses may be substantially constant when varying the first and/or second time intervals. When applying electrical pulses, the electrical pulses may remain unchanged, except for varying the first and/or second time intervals. The amplitude of the electrical pulses may be substantially constant when varying the first and/or second time intervals. Further, the electrical pulses may be varied by only varying the lengths of first time intervals between successive leading and trailing edges of the electrical pulses.

A train of two or more electrical pulses may be supplied in a row, wherein when applying the train of pulses, the train having a first electrical pulse at the start of the pulse train and having a second electrical pulse at the end of the pulse train, two or more pulse trains may be supplied in a row, wherein the lengths of the second time intervals between successive trailing edge of the second electrical pulse in a first pulse train and leading edge of the first electrical pulse of a second pulse train are varied.

When applying the electrical pulses, the electrical pulses may have a substantially constant current and a substantially constant voltage. The electrical pulses may also have a substantially constant current and a substantially constant voltage. Further, the electrical pulses may also have a substantially constant frequency. The electrical pulses within a pulse train may likewise have a substantially constant frequency.

The circuit formed by the first electric circuit and the external energy source may have a first characteristic time period or first time constant, and when effectively varying the transmitted energy, such frequency time period may be in the range of the first characteristic time period or time constant or shorter.

A system comprising an apparatus as described above is thus also provided for controlling transmission of wireless energy supplied to implanted energy consuming component of the apparatus. In it broadest sense, the system comprises a control device for controlling the transmission of wireless energy from an energy-transmission device, and an implantable internal energy receiver for receiving the transmitted wireless energy, the internal energy receiver being connected to implantable energy consuming component of the apparatus for directly or indirectly supplying received energy thereto. The system further comprises a determination device adapted to determine an energy balance between the energy received by the internal energy receiver and the energy used for the implantable energy consuming component of the apparatus, wherein the control device controls the transmission of wireless energy from the external energy-transmission device, based on the energy balance determined by the determination device.

Further, the system may comprise any of the following:
- A primary coil in the external energy source adapted to transmit the wireless energy inductively to a secondary coil in the internal energy receiver.
- The determination device is adapted to detect a change in the energy balance, and the control device controls the transmission of wireless energy based on the detected energy balance change
- The determination device is adapted to detect a difference between energy received by the internal energy receiver and energy used for the implantable energy consuming component of the apparatus, and the control device controls the transmission of wireless energy based on the detected energy difference.
- The control device controls the external energy-transmission device to decrease the amount of transmitted wireless energy if the detected energy balance change implies that the energy balance is increasing, or vice versa, wherein the decrease/increase of energy transmission corresponds to a detected change rate.
- The control device controls the external energy-transmission device to decrease the amount of transmitted wireless energy if the detected energy difference implies that the received energy is greater than the used energy, or vice versa, wherein the decrease/increase of energy transmission corresponds to the magnitude of said detected energy difference.
- The energy used for the apparatus is consumed to operate the apparatus, and/or stored in at least one energy storage device of the apparatus.
- Where electrical and/or physical parameters of the apparatus and/or physical parameters of the patient are determined, the energy-transmission device transmit the energy for consumption and storage according to a transmission rate per time unit which is determined by the determination device based on said parameters. The determination device also determines the total amount of transmitted energy based on said parameters.
- When a difference is detected between the total amount of energy received by the internal energy receiver and the total amount of consumed and/or stored energy, and the detected difference is related to the integral over time of at least one measured electrical parameter related to the energy balance, the determination device determines the integral for a monitored voltage and/or current related to the energy balance.
- When the derivative is determined over time of a measured electrical parameter related to the amount of consumed and/or stored energy, the determination device determines the derivative for a monitored voltage and/or current related to the energy balance.
- The energy-transmission device comprises a coil placed externally to the human body, and an electric circuit is provided to power the external coil with electrical pulses to transmit the wireless energy. The electrical pulses have leading and trailing edges, and the electric circuit is adapted to vary first time intervals between successive leading and trailing edges and/or second time intervals between successive trailing and leading edges of the electrical pulses to vary the power of the transmitted wireless energy. As a result, the energy receiver receiving the transmitted wireless energy has a varied power.

The electric circuit is adapted to deliver the electrical pulses to remain unchanged except varying the first and/or second time intervals.

The electric circuit has a time constant and is adapted to vary the first and second time intervals only in the range of the first time constant, so that when the lengths of the first and/or second time intervals are varied, the transmitted power over the coil is varied.

The electric circuit is adapted to deliver the electrical pulses to be varied by only varying the lengths of first time intervals between successive leading and trailing edges of the electrical pulses.

The electric circuit is adapted to supplying a train of two or more electrical pulses in a row, said train having a first electrical pulse at the start of the pulse train and having a second electrical pulse at the end of the pulse train, and the lengths of the second time intervals between successive trailing edge of the second electrical pulse in a first pulse train and leading edge of the first electrical pulse of a second pulse train are varied by the first electronic circuit The electric circuit is adapted to provide the electrical pulses as pulses having a substantially constant height and/or amplitude and/or intensity and/or voltage and/or current and/or frequency.

The electric circuit has a time constant, and is adapted to vary the first and second time intervals only in the range of the first time constant, so that when the lengths of the first and/or second time intervals are varied, the transmitted power over the first coil are varied.

The electric circuit is adapted to provide the electrical pulses varying the lengths of the first and/or the second time intervals only within a range that includes the first time constant or that is located relatively close to the first time constant, compared to the magnitude of the first time constant.

FIGS. 36-39 show in more detail block diagrams of four different ways of hydraulically or pneumatically powering an implanted apparatus according to the invention.

Figure 45:
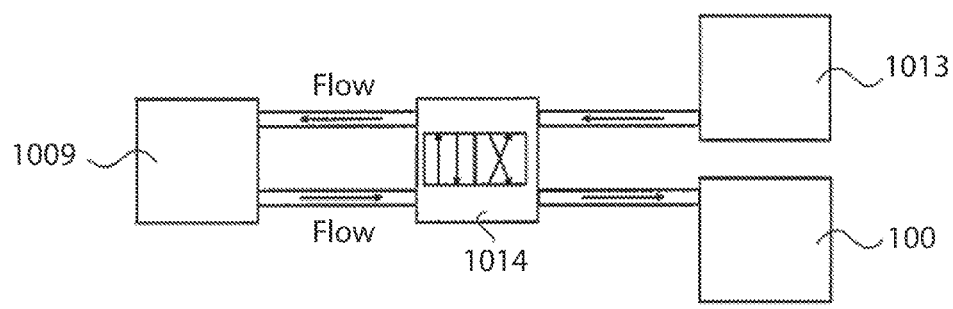
FIG. 45 is a more detailed block diagram of an arrangement for controlling the transmission of wireless energy used for the operation of the implanted assembly shown in FIG. 18.

FIG. 45 shows a system as described above with. The system comprises an implanted medical device 100 and further a separate regulation reservoir 1013, a one way pump 1009 and an alternate valve 1014.

Figure 46:
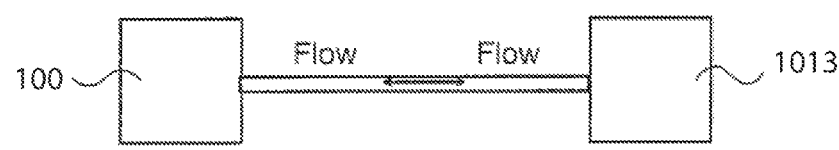
FIG. 46 is a circuit for the arrangement shown in FIG. 36, according to a possible implementation example.

FIG. 46 shows the implanted medical device 100 and a fluid reservoir 1013. By moving the wall of the regulation reservoir or changing the size of the same in any other different way, the adjustment of the apparatus may be performed without any valve, just free passage of fluid any time by moving the reservoir wall.

Figure 47:
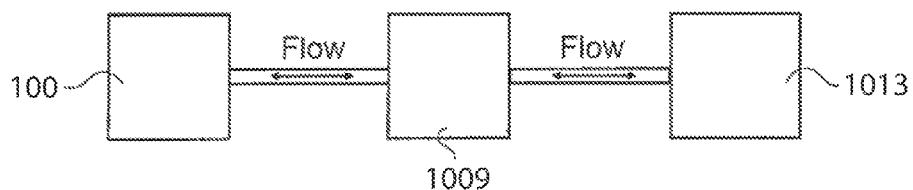
FIG. 47 shows the apparatus 1110, a two way pump 1009 and the regulation reservoir 1013.

FIG. 47 shows the apparatus 1110, a two way pump 1009 and the regulation reservoir 1013.

Figure 48:
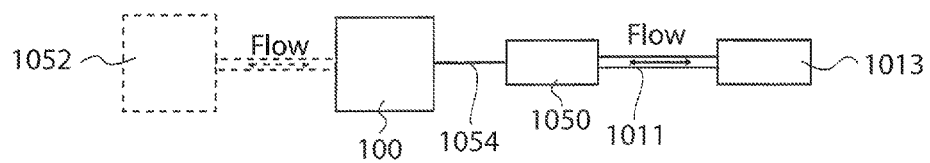
FIG. 48 shows a block diagram of a reversed servo system with a first closed system controlling a second closed system.

FIG. 48 shows a block diagram of a reversed servo system with a first closed system controlling a second closed system. The servo system comprises a regulation reservoir 1013 and a servo reservoir 1050. The servo reservoir 1050 mechanically controls an implanted medical device 100 via a mechanical interconnection 1054. The apparatus has an expandable/contactable cavity. This cavity is preferably expanded or contracted by supplying hydraulic fluid from the larger adjustable reservoir 1052 in fluid connection with the apparatus 10. Alternatively, the cavity contains compressible gas, which can be compressed and expanded under the control of the servo reservoir 1050.

The servo reservoir 1050 can also be part of the apparatus itself.

Figure 49:
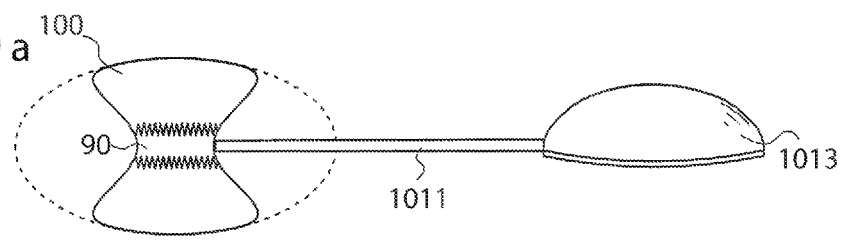
FIGS. 49a-c show a regulation reservoir placed subcutaneous under the patient's skin and is operated by pushing the outer surface thereof by means of a finger.
Figure 49:
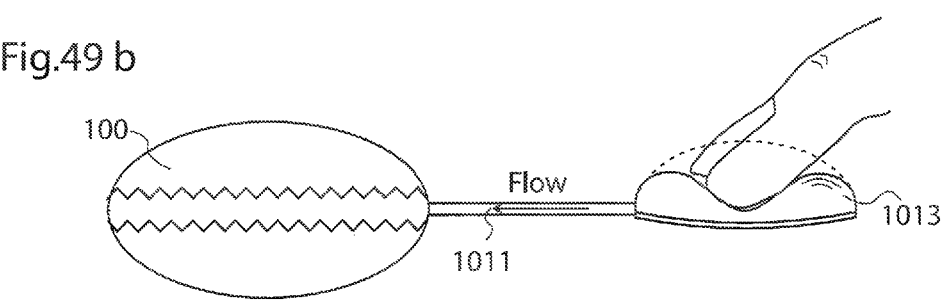
Figure 49:
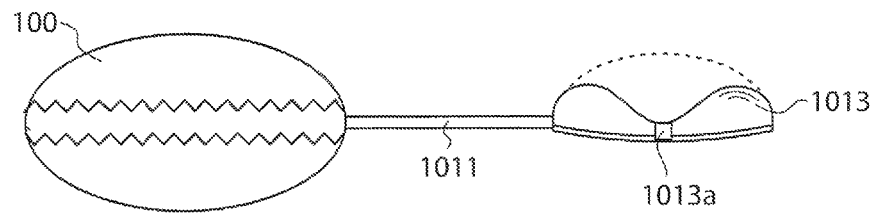

In one embodiment, the regulation reservoir is placed subcutaneous under the patients skin and is operated by pushing the outer surface thereof by means of a finger. This system is illustrated in FIGS. 49a-c. In FIG. 49a, a flexible subcutaneous regulation reservoir 1013 is shown connected to a bulge shaped servo reservoir 1050 by means of a conduit 1011. This bellow shaped servo reservoir 1050 is comprised in a flexible apparatus 1110. In the state shown in FIG. 49a, the servo reservoir 1050 contains a minimum of fluid and most fluid is found in the regulation reservoir 1013. Due to the mechanical interconnection between the servo reservoir 1050 and the apparatus 1110, the outer shape of the implanted medical device 100 is contracted, i.e., it occupies less than its maximum volume. This maximum volume is shown with dashed lines in the figure.

FIG. 49b shows a state wherein a user, such as the patient in with the apparatus is implanted, presses the regulation reservoir 1013 so that fluid contained therein is brought to flow through the conduit 1011 and into the servo reservoir 1050, which, thanks to its bellow shape, expands longitudinally. This expansion in turn expands the implanted medical device 100 so that it occupies its maximum volume, thereby stretching the stomach wall (not shown), which it contact.

The regulation reservoir 1013 is preferably provided with means 1013a for keeping its shape after compression. This means, which is schematically shown in the figure, will thus keep the implanted medical device 100 in a stretched position also when the user releases the regulation reservoir. In this way, the regulation reservoir essentially operates as an on/off switch for the system.

Figure 50:
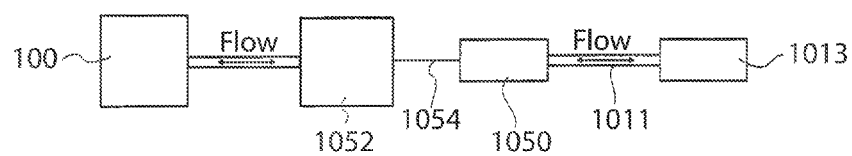
FIG. 50 shows a first closed system controlling a second closed system.

An alternative embodiment of hydraulic or pneumatic operation will now be described with reference to FIGS. 41 and 42a-c. The block diagram shown in FIG. 50 comprises with a first closed system controlling a second closed system. The first system comprises a regulation reservoir 1013 and a servo reservoir 1050. The servo reservoir 1050 mechanically controls a larger adjustable reservoir 1052 via a mechanical interconnection 1054. An implanted medical device 100 having an expandable/contactable cavity is in turn controlled by the larger adjustable reservoir 1052 by supply of hydraulic fluid from the larger adjustable reservoir 1052 in fluid connection with the apparatus 1110.

Figure 51A:
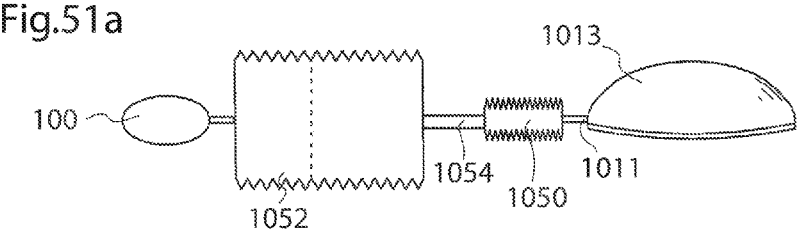
FIG. 51a-c show an implanted medical device 100 having an expandable/contactable cavity is in turn controlled by the larger adjustable reservoir 1052 by supply of hydraulic fluid from the larger adjustable reservoir 1052 in fluid connection with the apparatus 1110.
Figure 51B:
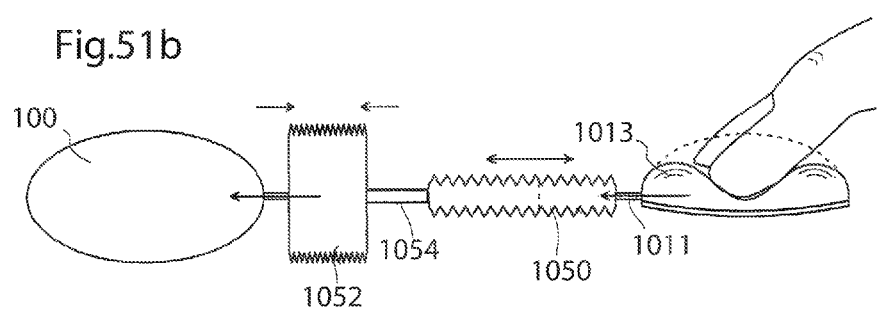
Figure 51C:
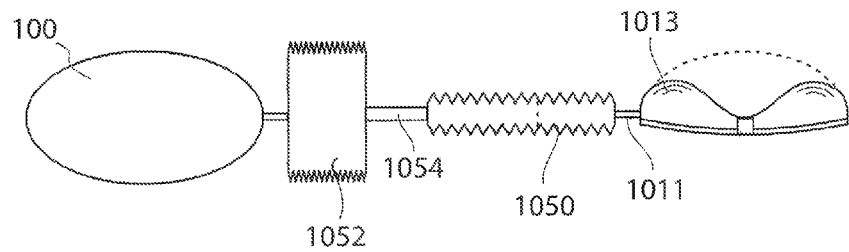

An example of this embodiment will now be described with reference to FIG. 51a-c. Like in the previous embodiment, the regulation reservoir is placed subcutaneous under the patient's skin and is operated by pushing the outer surface thereof by means of a finger. The regulation reservoir 1013 is in fluid connection with a bellow shaped servo reservoir 1050 by means of a conduit 1011. In the first closed system 1013, 1011, 1050 shown in FIG. 51a, the servo reservoir 1050 contains a minimum of fluid and most fluid is found in the regulation reservoir 1013.

The servo reservoir 1050 is mechanically connected to a larger adjustable reservoir 1052, in this example also having a bellow shape but with a larger diameter than the servo reservoir 1050. The larger adjustable reservoir 1052 is in fluid connection with the apparatus 1110. This means that when a user pushes the regulation reservoir 1013, thereby displacing fluid from the regulation reservoir 1013 to the servo reservoir 1050, the expansion of the servo reservoir 1050 will displace a larger volume of fluid from the larger adjustable reservoir 1052 to the apparatus 10. In other words, in this reversed servo, a small volume in the regulation reservoir is compressed with a higher force and this creates a movement of a larger total area with less force per area unit.

Like in the previous embodiment described above with reference to FIGS. 40a-c, the regulation reservoir 1013 is preferably provided with means 1013a for keeping its shape after compression. This means, which is schematically shown in the figure, will thus keep the implanted medical device 100 in a stretched position also when the user releases the regulation reservoir. In this way, the regulation reservoir essentially operates as an on/off switch for the system.

The control assembly can be placed in the body of a patient by different methods. One method comprises the steps of:
inserting a needle or tube like instrument into the abdomen of the patients body,
using the needle or tube like instrument to fill the abdomen with gas thereby expanding the abdominal cavity,
placing at least two laparoscopic trocars in the patients body,
inserting a camera through one of the trocars into the abdomen,
inserting at least one dissecting tool through a trocar and dissecting an area of a body tissue of the patient,
placing a first unit of the control assembly at a first side of the body tissue of the patient,
placing a second unit of the control assembly at a second side of the body tissue of the patient, and
placing an interconnecting device adapted for mechanical interconnection of the first and second unit to keep the assembly in place by the body tissue, the interconnecting device having a cross-sectional area which is smaller than the cross-sectional area of the first unit and the second unit in a plane parallel to the extension of the body tissue.

Another method for placing a control assembly in a human or mammal patient comprises the steps of:
cutting the skin of the patient
dissecting an area of a body tissue,
placing a first unit of the control assembly at a first side of the body tissue of the patient,
placing a second unit of the control assembly at a second side of the body tissue of the patient, and
placing an interconnecting device adapted for mechanical interconnection of the first and second unit to keep the assembly in place by the body tissue, the interconnecting device having a cross-sectional area which is smaller than the cross-sectional area of the first unit and the second unit in a plane parallel to the extension of the body tissue.

Please note that any embodiment or part of embodiment as well as any method or part of method could be combined in any way. All examples herein should be seen as part of the general description and therefore possible to combine in any way in general terms.

The invention claimed is:

1. An implantable medical device for lubrication of a synovial joint having a joint cavity, wherein said implantable device comprises:
a solid lubricant,
an implantable replaceable cartridge adapted to have an opening into the joint cavity, when implanted,
an implantable mechanical feeding device, wherein said implantable mechanical feeding device is adapted to feed said solid lubricant into the joint cavity for lubricating the synovial joint, and wherein the mechanical feeding device is adapted to propel the solid lubricant, thereby feeding the solid lubricant into the joint, when implanted, and
a system for manually and non-invasively controlling the medical device, comprising at least one of;
at least one switch implantable in the patient,
a wireless remote control, and
an implantable hydraulic reservoir which is hydraulically connected to the implantable medical device and adapted to be regulated by manually pressing the hydraulic reservoir, wherein the system further comprises a sensor and/or a measuring device for sensing or measuring at least one of:
at least one physical parameter of the patient, and
at least one functional parameter related to the implantable medical device and comprising at least one of: a functional parameter correlated to a transfer of energy for charging an internal energy source, and a functional parameter related to the implantable medical device,
wherein the implantable medical device further comprises a feedback device for sending feedback information from inside the patient's body to at least one of:
an implantable internal control unit,
an external control unit outside of the patient's body,
an external control unit outside of the patient's body, via the internal control unit, and
an external control unit outside of the patient's body, via the internal control unit according to a programming of the internal control unit performed by the external control unit,
wherein the feedback information is related to at least one of: the at least one physical parameter of the patient and the at least one functional parameter related to the implantable medical device.

2. The implantable medical device according to claim 1, wherein said solid lubricant has shear thinning properties, such that the viscosity of said solid lubricant is reduced when said solid lubricant is exposed to strain in the joint cavity.

3. The implantable medical device according to claim 1, wherein said solid lubricant comprises at least one of:
high-molecular weight hyaluronic acid,
crosslinked high-molecular weight hyaluronic acid, and
hyaluronic acid of at least two different high-molecular weights, crosslinked to form a solid gel.

4. The implantable medical device according to claim 1, wherein said solid lubricant comprises a crosslinking agent chosen from 1,2,3,4-diepoxybutane, divinyl sulfone.

5. The implantable medical device according to claim 1, wherein said solid lubricant comprises a hydrophilic polymer chosen from synthetic and natural polysaccharides.

6. The implantable medical device according to claim 5, wherein said hydrophilic polymer comprises a hydrophilic polymer selected from a group consisting of:
a. hydroxyethyl cellulose,
b. camoxymethyl cellulose,
c. xanthan gum,
d. chondroitin sulfate,
e. heparin,
f. protein,
g. sulfated protein,
h. synthetic water-soluble polymers.

7. The implantable medical device according to claim 6, wherein said protein comprises a protein selected from a group consisting of:
a. collagen,
b. elastin, c. albumin, and
d. a globulin.

8. The implantable medical device according to claim 6, wherein said sulfated protein comprises a sulfated protein selected from a group consisting of:
   a. keratin sulfate, and
   b. sulfated aminoglycosaminoglycans.

9. The implantable medical device according td claim 6, wherein said synthetic water-soluble polymer is a synthetic water-soluble polymer selected from a group consisting of:
   a. polyvinyl alcohol,
   b. co-polymers of polyvinyl alcohol, and
   c. co-polymers of poly-(hydroxyethyl)methacrylate.

10. The implantable medical device according to claim 1, wherein said medical device is adapted to be implanted in the area of the hip joint, such that said solid lubricant can be inserted into the joint cavity of the hip joint.

11. The implantable medical device according to claim 10, wherein said medical device is adapted to at least partially be implanted in the caput femur, such that the feeding device can feed the solid lubricant into the hip joint cavity, towards the acetabulum.

12. The implantable medical device according to claim 10, wherein the implantable device is adapted to be inserted into a bore in the femoral bone.

13. The implantable medical device according to claim 10, wherein said medical device is adapted to at least partially be implanted in the pelvis, such that the feeding device can feed the solid lubricant into the hip joint cavity, towards the caput femur.

14. The implantable medical device according to claim 1, further comprising a retention member for retaining the medical device inside of a bore, wherein said retention member comprises at least one of; at least one bone contacting portion adapted to press on the bone of the inside of the bore for retaining said medical device in the bore, and at least one spring member adapted to exert force on said at least one bone contacting portion.

15. The implantable medical device according to claim 1, wherein said feeding device comprises at least one of;
   an energized feeding device,
   an energized feeding device comprising a motor,
   an elastic member,
   an elastic member being a spring member, and
   an adaptation to be powered by a pressurized gaseous fluid.

16. The implantable medical device according to claim 1, wherein said medical device comprises a cartridge being adapted to be exchanged when said solid lubricant housed inside said cartridge has been used up.

17. The implantable medical device according to claim 1, wherein the implantable medical device further comprises an implantable sleeve adapted to be placed within a bone of the patient, and further adapted to receive said implantable medical device.

18. The implantable medical device according to claim 1, further comprising a system, comprising at least one of;
   an internal energy source for powering the implantable medical device, and
   an internal energy receiver and an adaptation to be energized non-invasively and wirelessly by an energy transmission device from outside the patient's body, wherein the energy transmission device is adapted for sending wireless energy to at least one of:
      an implantable internal energy source or energy storage comprised in the system, being chargeable by the energy transferred from the energy transmission device, and
      at least one implantable energy consuming component of the system being energized with the wireless energy.

* * * * *